(12) United States Patent
Yang et al.

(10) Patent No.: US 8,168,752 B2
(45) Date of Patent: May 1, 2012

(54) T CELL PROTEINS AND NUCLEOTIDES ENCODING THE SAME

(75) Inventors: Jianfei Yang, Sandy Hook, CT (US); Frank James King, New Milford, CT (US); Jun Li, Danbury, CT (US); Zhenhao Qi, Sandy Hook, CT (US); Ming Xue, Newtown, CT (US)

(73) Assignee: Boehringer Ingelheim Pharmaceutical, Inc., Ridgefield, CT (US)

(*) Notice: Subject to any disclaimer, the term of this patent is extended or adjusted under 35 U.S.C. 154(b) by 21 days.

(21) Appl. No.: 12/573,992

(22) Filed: Oct. 6, 2009

(65) Prior Publication Data

US 2010/0036100 A1 Feb. 11, 2010

Related U.S. Application Data

(62) Division of application No. 11/262,688, filed on Oct. 31, 2005, now abandoned.

(60) Provisional application No. 60/624,605, filed on Nov. 3, 2004.

(51) Int. Cl.
C07K 14/54 (2006.01)
(52) U.S. Cl. ............... 530/351; 435/252.3; 435/69.1
(58) Field of Classification Search .................. None
See application file for complete search history.

(56) References Cited

U.S. PATENT DOCUMENTS

| 7,064,186 B2 | 6/2006 | Sprecher et al. |
| 2003/0215838 A1 | 11/2003 | Sprecher et al. |

FOREIGN PATENT DOCUMENTS

| WO | 03060090 A | 7/2003 |
| WO | 2005063986 | 7/2005 |

OTHER PUBLICATIONS

Gardella, Stefania, et al; Interleukin-18 Synthesis and Secretion by Dendritic Cells are Modulated by Interaction with Antigen-Specific T Cells; Journal of Leukocyte Biology (1999) vol. 66 pp. 237-241.
Gardella, Stefania, et al; The Nuclear Protein HMGB1 is Secreted by Monocytes Via a Non-Classical, Vesicle-Mediated Secretory Pathway; Europeam Molecular Biology Organization Reports (2002) vol. 3, No. 10 pp. 995-1001.
Gerashchenko, Maxim V. et al; CUG Start Codon Generates Thioredoxin/Glutathione Reductase Isoforms in Mouse Testes; Journal of Biological Chemistry (2010) vol. 285, No. 7 pp. 4595-4602.
Haskill, Stephen, et al; cDNA Cloning of an Intracellular Form of the Human Interleukin 1 Receptor Antagonist Associated with Epithelium; Proc. Natl. Acad. Sci. USA (1991) vol. 88 pp. 3681-3685.
Kleemann, Robert, et al; Intracellular Action of the Cytokine MIF to Modulate AP-1 Activity and the Cell Cycle Through Jab1; Nature (2000) vol. 408 pp. 211-216.

Kozak, Marilyn; Interpreting cDNA Sequences: Some Insights from Studies on Translation; Mammalian Genome (1996) vol. 7 pp. 563-574.
Kozak, Marilyn; Recognition of AUG and Alternative Initiator Codons is Augmented by G in Position +4 but is not Generally Affected by the Nucleotides in Positions +5 and +6; The EMOB Journal (1997) vol. 16, No. 9 pp. 2482-2492.
Orinska, Zane, et al; IL-15 Constrains Mast Cell-Dependent Antibacterial Defenses by Suppressing Chymase Activities; Nature Medicine (2007) vol. 13 pp. 927-934.
European Search Report of Jun. 16, 2008 incorporating International Preliminary Report on Patentability and Written Opinion of the ISA dated May 8, 2007 of PCT/US20005/039088.
C. Diveu, at al.,"Predominant Expression of the Long Isoform of GP130like (GPL) Receptor is Required for Interleukin-31 Signaling". Eur Cytokine Netw., vol. 15, No. 4, 2004 p. 291 XP002397783.
A. Hammond, et al, "Orphan Class 1 Cytokine Receptor ZCYTOR17 is Up-Regulated in Activated monocytes and T-Cells" XP002397782, Journal of Interferon & Cytokine Res., 2002, 22 (supplement 1) : p. S-48.
S.R. Dillon, et, al. "Interleukin 31. a Cylokine Produced by Activated T Cells, Induces Dermatitis in Mice", Nature Immunology. vol. 5, No. 7, 2004. p. 752-760.
N. Watanabe. et al., "BTLA is a Lymphocyte Inhibitory Receptor with Similarities to CTLA-4 and PD-1", Nature Immunology, vol. 4, No. 7, 2003, p. 670.
G. M Wahl, et al., "Molecular Hybridization of Immobilized Nucleic Acids: Theoretical Concepts and Practical Considerations", Methods in Enzymology, vol. 152, 1987, p. 399.
A R. Kimmel "Identification and Characterization of Specific Clones: Strategy for Confirming the Validity of Presumptive Clones", Methods in Enzymology. vol. 152, 1987, p. 507.
SM. Elbashir, et al., "Duplexes of 21-Nucleotide RNAs Mediate RNA Interference in Cultured Mammalian Cells", Nature, vol. 411, 2001, p. 494.
W.J. Sandborn, M.D., et al., Infliximab in the Treatment of Crohn's Disease: A Users Guide for Clinicians. Am. Journal of Gastroenterology. vol. 97, No. 12, 2002, p. 2962.
IUPAC-IUB Commission an Biochemical Nomenclature Symbols for Amino-Acid Derivatives and Peptides Recommendations (1971), Biochemistry, vol. 11, No. 9, 1972, p. 1726.
D.G Higgins, et al., "CLUSTAL: A Package for Performing Multiple Sequence Alignment on a Microcomputer", Gene, vol. 73, 1988, p. 237.
J. Hein. "Unified Approach to Alignment and Phylogenies", Methods in Enzymology, vol. 183, 1990 p. 626.
Database uniprot [online] Aug. 16, 2004. "Interleukin 31" XP002381280 retrieved from EBI accession No. Uniport: Q6EAL8 100% sequence identity with sequence ID No. 2.
Office Action of co-peding U.S. Appl. No. 11/262,688 dated, Apr. 16, 2009.
Marilyn Kozak, Gene. Oct. 16, 2002;299(1-2):1-34.

*Primary Examiner* — Zachary Skelding
(74) *Attorney, Agent, or Firm* — Michael P. Morris; Edward S. Lazer

(57) ABSTRACT

The present invention relates to mouse and human J12 polynucleotides, polypeptide and anti J12 antibody molecules. The J12 is a cytokine that is preferentially expressed in Th2 cells. The polypeptides and/or antibodies described herein can be used in methods for detection and treatment of certain autoimmune and inflammatory diseases including asthma.

4 Claims, 22 Drawing Sheets

Fig. 1-1

Alignment of mouse J12 cDNA sequence with EST AK005939

```
Alignment of AK005939 vs Mouse J12

1                                                  50
    AK005939      (1)   ---------------------------------------GGCCTTCTCCTTAT
    Mouse J12     (1)   AGAACGCAAGGACAAGGGCAGGCCCTGGAGCACAGATGCCTTCTCCTTAT
    Consensus     (1)                                          GCCTTCTCCTTAT
                        51                                                100
    AK005939     (15)   GCCTTCCCTGTGTTCACTAGAGCCATCCCCCTGCCTCCGGAATTCCCACA
    Mouse J12    (51)   GCCTTCCCTGTGTTCACTAGAGCCATCCCCCTGCCTCCGGAATTCCCACA
    Consensus    (51)   GCCTTCCCTGTGTTCACTAGAGCCATCCCCCTGCCTCCGGAATTCCCACA
                        101                                               150
    AK005939     (65)   GATGGATCGCTCTGTGGCTTCTTAAAACTTCCCTGCAGGGCACTGACCCT
    Mouse J12   (101)   GATGGATCGCTCTGTGGCTTCTTAAAACTTCCCTGCAGGGCACTGACCCT
    Consensus   (101)   GATGGATCGCTCTGTGGCTTCTTAAAACTTCCCTGCAGGGCACTGACCCT
                        151                                               200
    AK005939    (115)   CAGCCCCTCTAAGTCACTTCTTCCCCAGTGATTGTACTTTTCAATCGGGC
    Mouse J12   (151)   CAGCCCCTCTAAGTCACTTCTTCCCCAGTGATTGTACTTTTCAATCGGGC
    Consensus   (151)   CAGCCCCTCTAAGTCACTTCTTCCCCAGTGATTGTACTTTTCAATCGGGC
                        201                                               250
    AK005939    (165)   TTCAAACTTTCCTCTCATTAAATCAGCAAGCACTTTCCAAGAAAAGAGAG
    Mouse J12   (201)   TTCAAACTTTCCTCTCATTAAATCAGCAAGCACTTTCCAAGAAAAGAGAG
    Consensus   (201)   TTCAAACTTTCCTCTCATTAAATCAGCAAGCACTTTCCAAGAAAAGAGAG
                        251                                               300
    AK005939    (215)   ATGCTCAAGATGCCTTCCTGTGTG--------------------------
    Mouse J12   (251)   ATGCTCAAGATGCCTTCCTGTGTGCCCTGCTTTCCCCAGGCCGAGCCGAG
    Consensus   (251)   ATGCTCAAGATGCCTTCCTGTGTG
                        301                                               350
    AK005939    (239)   --------------------------------------------------
    Mouse J12   (301)   GCTGGCAACCTTTTGAAAATGTTTTCTGGAGAAAAGCTGAGCAATGGTTT
    Consensus   (301)
                        351                                               400
    AK005939    (239)   --------------------------------------------------
    Mouse J12   (351)   TGCCATGGGCGGGCCTTTGATCTGCTTCCTCATGACAACCCTTTATATAT
    Consensus   (351)
                        401                                               450
    AK005939    (239)   --------------------------------------------------
    Mouse J12   (401)   TGCCTGGTGGCCATGGCGAACACACCAGGCTCCAGAGACCACAGGCAAAG
    Consensus   (401)
                        451                                               500
    AK005939    (239)   ---------------------------------------------GAACA
    Mouse J12   (451)   CGGGCCTTCCTCACTCTCTTACCGTCGCCATGATCTTCCACACAGGAACA
    Consensus   (451)                                                GAACA
                        501                                               550
    AK005939    (244)   ACGAAGCCTACCCTGGTGCTGCTTTGCTGTATAGGAACCTGGCTGGCCAC
    Mouse J12   (501)   ACGAAGCCTACCCTGGTGCTGCTTTGCTGTATAGGAACCTGGCTGGCCAC
    Consensus   (501)   ACGAAGCCTACCCTGGTGCTGCTTTGCTGTATAGGAACCTGGCTGGCCAC
                        551                                               600
    AK005939    (294)   CTGCAGCTTGTCCTTCGGTGCCCCAATATCGAAGGAAGACTTAAGAACTA
    Mouse J12   (551)   CTGCAGCTTGTCCTTCGGTGCCCCAATATCGAAGGAAGACTTAAGAACTA
    Consensus   (551)   CTGCAGCTTGTCCTTCGGTGCCCCAATATCGAAGGAAGACTTAAGAACTA
                        601                                               650
    AK005939    (344)   CAATTGACCTCTTGAAACAAGAGTCTCAGGATCTTTATAACAACTATAGC
```

Fig. 1-2

```
Mouse J12    (601)  CAATTGACCTCTTGAAACAAGAGTCTCAGGATCTTTATAACAACTATAGC
Consensus    (601)  CAATTGACCTCTTGAAACAAGAGTCTCAGGATCTTTATAACAACTATAGC
                    651                                              700
AK005939     (394)  ATAAAGCAGGCATCTGGGATGTCAGCAGACGAATCAATACAGCTGCCGTG
Mouse J12    (651)  ATAAAGCAGGCATCTGGGATGTCAGCAGACGAATCAATACAGCTGCCGTG
Consensus    (651)  ATAAAGCAGGCATCTGGGATGTCAGCAGACGAATCAATACAGCTGCCGTG
                    701                                              750
AK005939     (444)  TTTCAGCCTGGACCGGGAAGCATTAACCAACATCTCGGTCATCATAGCAC
Mouse J12    (701)  TTTCAGCCTGGACCGGGAAGCATTAACCAACATCTCGGTCATCATAGCAC
Consensus    (701)  TTTCAGCCTGGACCGGGAAGCATTAACCAACATCTCGGTCATCATAGCAC
                    751                                              800
AK005939     (494)  ATCTGGAGAAAGTCAAAGTGTTGAGCGAGAACACAGTAGATACTTCTTGG
Mouse J12    (751)  ATCTGGAGAAAGTCAAAGTGTTGAGCGAGAACACAGTAGATACTTCTTGG
Consensus    (751)  ATCTGGAGAAAGTCAAAGTGTTGAGCGAGAACACAGTAGATACTTCTTGG
                    801                                              850
AK005939     (544)  GTGATAAGATGGCTAACAAACATCAGCTGTTTCAACCCACTGAATTTAAA
Mouse J12    (801)  GTGATAAGATGGCTAACAAACATCAGCTGTTTCAACCCACTGAATTTAAA
Consensus    (801)  GTGATAAGATGGCTAACAAACATCAGCTGTTTCAACCCACTGAATTTAAA
                    851                                              900
AK005939     (594)  CATTTCTGTGCCTGGAAATACTGATGAATCCTATGATTGTAAAGTGTTCG
Mouse J12    (851)  CATTTCTGTGCCTGGAAATACTGATGAATCCTATGATTGTAAAGTGTTCG
Consensus    (851)  CATTTCTGTGCCTGGAAATACTGATGAATCCTATGATTGTAAAGTGTTCG
                    901                                              950
AK005939     (644)  TGCTTACGGTTTTAAAGCAGTTCTCAAACTCCATGGCAGAACTCCAGGCT
Mouse J12    (901)  TGCTTACGGTTTTAAAGCAGTTCTCAAACTGCATGGCAGAACTGCAGGCT
Consensus    (901)  TGCTTACGGTTTTAAAGCAGTTCTCAAACTGCATGGCAGAACTGCAGGCT
                    951                                             1000
AK005939     (694)  AAGGACAATACTACATGCTGAGTGATGGGGCGGGGGGGTGCACTGTCCT
Mouse J12    (951)  AAGGACAATACTACATGCTGAGTGATGGGGCGGGGGGGGTGCACTGTCCT
Consensus    (951)  AAGGACAATACTACATGCTGAGTGATGGGGCGGGGGGGGTGCAGTGTCCT
                    1001                                            1050
AK005939     (744)  CAGCAGTGCCTGTCCTTCGAGGGCTGAGCTTGCAACCCAGGACTTAACTC
Mouse J12   (1001)  CAGCAGTGCCTGTCCTTCGAGGGCTGAGCTTGCAACCCAGGACTTAACTC
Consensus   (1001)  CAGCAGTGCCTGTCCTTCGAGGGCTGAGCTTGCAACCCAGGACTTAACTC
                    1051                                            1100
AK005939     (794)  CAAAGGGACTGTGCGGTCATTACTAGTCATGTTATTTATGTTTTTATTTT
Mouse J12   (1051)  CAAAGGGACTGTGCGGTCATTACTAGTCATGTTATTTATGTTTTTATTTT
Consensus   (1051)  CAAAGGGACTGTGCGGTCATTACTAGTCATGTTATTTATGTTTTTATTTT
                    1101                                            1150
AK005939     (844)  GTCCACTGAAATCTTGTTCTGCTACCCTGTAGGGACTGGAAGTGGCAGCT
Mouse J12   (1101)  GTCCACTGAAATCTTGTTCTGCTACCCTGTAGGGACTGGAAGTGGCAGCT
Consensus   (1101)  GTCCACTGAAATCTTGTTCTGCTACCCTGTAGGGACTGGAAGTGGCAGCT
                    1151                                            1200
AK005939     (894)  ATATTTATTTATTTATGTACTGAGTTTGTTAACGCTCCATGGAGGAGCCT
Mouse J12   (1151)  ATATTTATTTATTTATGTACTGAGTTTGTTAACGCTCCATGGAGGAGCCT
Consensus   (1151)  ATATTTATTTATTTATGTACTGAGTTTGTTAACGCTCCATGGAGGAGCCT
                    1201                                            1249
AK005939     (944)  TCAGAGTCTATTTAATAAATTATATTGACATG------------------
Mouse J12   (1201)  TCAGAGTCTATTTAATAAATTATATTGACATGAAAAAAAAAAAAAAAAAA
Consensus   (1201)  TCAGAGTCTATTTAATAAATTATATTGACATG
```

Fig. 2-1
A) Mouse J12 protein sequence and cleavage site
MIFHTGTTKPTLVLLCCIGTWLATCSLSFGAPISKEDLRTTIDLLKQESQ
DLYNNYSIKQASGMSADESIQLPCFSLDREALTNISVIIAHLEKVKVLSEN
TVDTSWVIRWLTNISCFNPLNLNISVPGNTDESYDCKVFVLTVLKQFSN
CMAELQAKDNTTC
B) Mouse J12 gene structure vs. AK005939
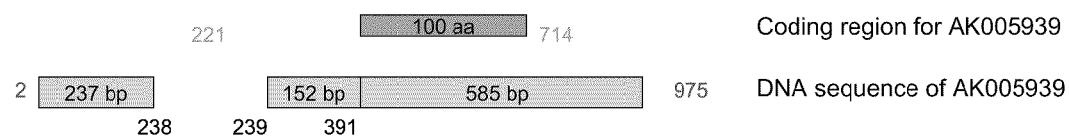
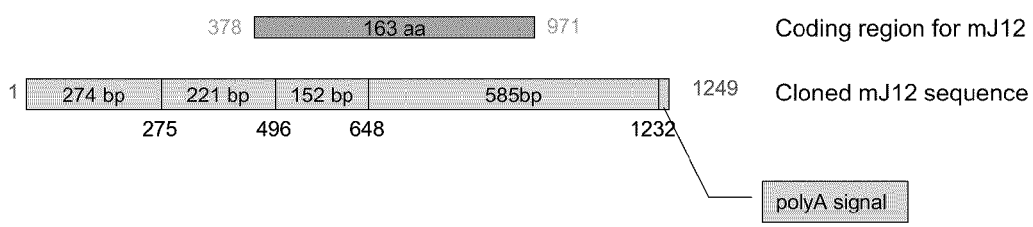

C) Mouse J12 gene Genomic structure

GeneChip results showed J12 mRNA is specifically induced
in mouse Th2 cells by anti-CD3 stimulation TaqMan PCR confirmed J12 mRNA is specifically induced in mouse Th2 cells by anti-CD3 stimulation Mouse J12 mRNA expression in normal tissues

Fig 6

Human J12 sequences:

A) Human J12 var1

GRGLSRRSHLPRGKSPPSGSDSLAPTTCVFSSALIYKNGITAGGSKCGSSR
RHSFLHASDPHVRQPTVCLQLSIHNTSHSLCQKLNQAGHVACTYSRSTLG
GQGSHGEHIWLQKPPLKLALLSLAMASHSGPSTSVLFLFCCLGGWLASHT
LPVRLLRPSDDVQKIVEELQSLSKMLLKDVEEEKGVLVSQNYTLPCLSPD
AQPPNNIHSPAIRAYLKTIRQLDNKSVIDEIIEHLDKLIFQDAPETNISVPTD
THECKRFILTISQQFSECMDLALKSLTSGAQQATT

B) Human J12 var2

Predicted cleavage
                site of signal peptide
                      ↓

MASHSGPSTSVLFLFCCLGGWLASHTLPVRLLRPSDDVQKIVEEL
QSLSKMLLKDVEEEKGVLVSQNYTLPCLSPDAQPPNNIHSPAIRA
YLKTIRQLDNKSVIDEIIEHLDKLIFQDAPETNISVPTDTHECKRFILT
ISQQFSECMDLALKSLTSGAQQATT

C) Human J12 var3

MEACPRAPHDFHTSHCSSLTGLQFYLPQYLDGTHIYICSSFLHASDPHVR
QPTVCLQLSIHNTSHSLCQKLNQAGHVACTYSRSTLGGQGSHGEHIWLQ
KPPLKLALLSLAMASHSGPSTSVLFLFCCLGGWLASHTLPVRLLRPSDDV
QKIVEELQSLSKMLLKDVEEEKGVLVSQNYTLPCLSPDAQPPNNIHSPAIR
AYLKTIRQLDNKSVIDEIIEHLDKLIFQDAPETNISVPTDTHECKRFILTISQ
QFSECMDLALKSLTSGAQQATT

Fig. 7
A) Human J12 splicing variants gene structure
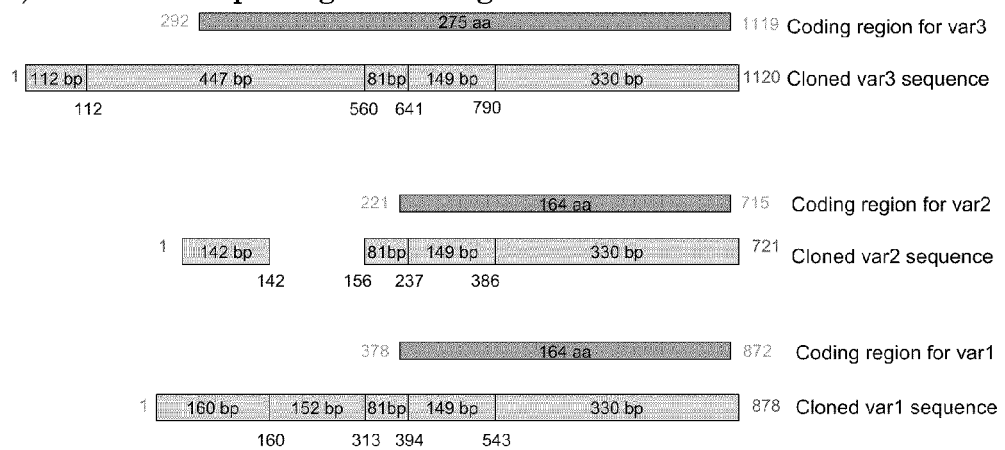
B) Human J12 gene structure:
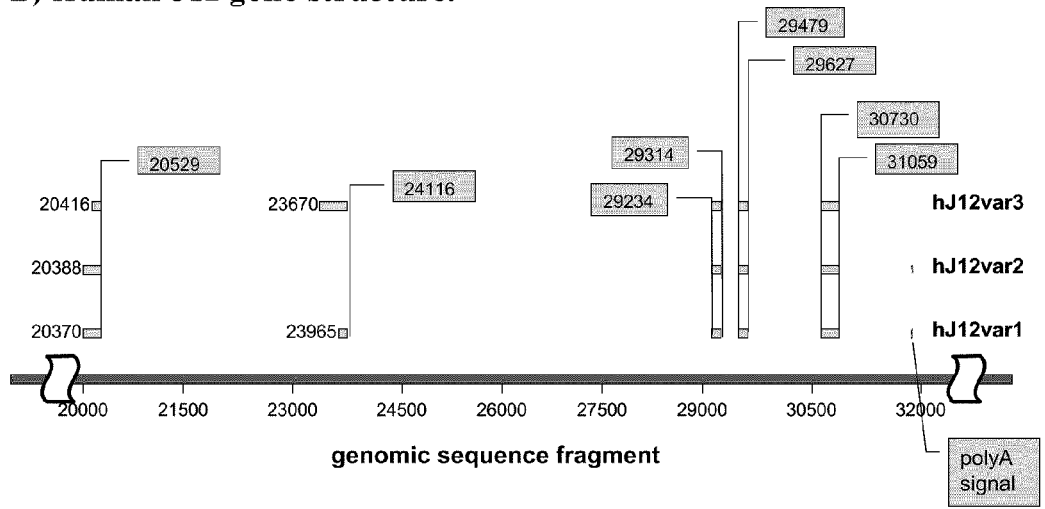

Fig. 8

SMART sequence analysis of human J12_var1, J12_var2 and J12_var3 protein sequences

J12 var1 results

| name | begin | end | E-value | reason |
|---|---|---|---|---|
| WR1 | 45 | 84 | 1.21e+03 | threshold |
| AAI | 47 | 155 | 1.30e+03 | threshold |
| DSL | 56 | 110 | 3.19e+03 | threshold |
| SR | 63 | 142 | 4.00e+03 | threshold |
| GAL4 | 63 | 104 | 1.54e+03 | threshold |
| Knot1 | 68 | 98 | 2.95e+03 | threshold |
| IL6 | 77 | 224 | 7.33e+02 | threshold |
| ZnF_C2HC | 81 | 95 | 1.45e+03 | threshold |
| Kelch | 93 | 131 | 2.60e+03 | threshold |
| ANATO | 116 | 142 | 2.86e+03 | threshold |
| ZU5 | 132 | 220 | 2.13e+02 | threshold |
| IL4_13 | 133 | 274 | 4.79e+01 | threshold |
| RhoGAP | 134 | 270 | 2.70e+03 | threshold |
| CSF2 | 148 | 269 | 3.83e+03 | threshold |
| CLH | 154 | 285 | 1.27e+05 | threshold |
| BAG | 159 | 240 | 1.44e+03 | threshold |
| DSRM | 166 | 224 | 1.31e+03 | threshold |
| EZ_HEAT | 211 | 239 | 2.90e+03 | threshold |

J12 var2 results

| name | begin | end | E-value |
|---|---|---|---|
| signal peptide | 1 | 25 | - |
| ZU5 | 7 | 95 | 2.13e+02 |
| IL4_13 | 8 | 149 | 4.79e+01 |
| RhoGAP | 9 | 145 | 2.70e+03 |
| transmembrane | 10 | 32 | - |
| CSF2 | 23 | 144 | 3.83e+03 |
| CLH | 29 | 160 | 1.27e+05 |
| BAG | 34 | 115 | 1.44e+03 |
| IL6 | 38 | 156 | 9.52e+02 |
| DSRM | 41 | 99 | 1.31e+03 |
| EZ_HEAT | 86 | 114 | 2.90e+03 |

J12 var3 results

| name | begin | end | E-value | reason |
|---|---|---|---|---|
| TGFB | 4 | 82 | 1.42e+02 | threshold |
| Ubox | 14 | 71 | 2.33e+03 | threshold |
| WR1 | 36 | 70 | 1.80e+03 | threshold |
| AAI | 38 | 141 | 8.78e+02 | threshold |
| DSL | 42 | 96 | 3.19e+03 | threshold |
| SR | 49 | 128 | 4.00e+03 | threshold |
| GAL4 | 49 | 90 | 1.54e+03 | threshold |
| Knot1 | 54 | 84 | 2.95e+03 | threshold |
| IL6 | 63 | 210 | 7.33e+02 | threshold |
| ZnF_C2HC | 67 | 81 | 1.45e+03 | threshold |
| Kelch | 79 | 117 | 2.60e+03 | threshold |
| ANATO | 102 | 128 | 2.86e+03 | threshold |
| ZU5 | 118 | 206 | 2.13e+02 | threshold |
| IL4_13 | 119 | 260 | 4.79e+01 | threshold |
| RhoGAP | 120 | 256 | 2.70e+03 | threshold |
| CSF2 | 134 | 255 | 3.83e+03 | threshold |
| CLH | 140 | 271 | 1.27e+05 | threshold |
| BAG | 145 | 226 | 1.44e+03 | threshold |
| DSRM | 152 | 210 | 1.31e+03 | threshold |
| EZ_HEAT | 197 | 225 | 2.90e+03 | threshold |

Fig. 9-1

Alignment of the EST AK005939 and human J12 variants

Alignment of AK005939 vs human J12 var1, var2, and var3

```
                          1                                                  50
  AK005939       (1)   --------------------------------------------------
  hJ12 var1      (1)   --------------------------------------------------
  hJ12 var2      (1)   --------------------------------------------------
  hJ12 var3      (1)   CCCCATCCGGATCAGACAGCCTGGCCCCAACCACCTGCGTTTTCTCTTCT
  Consensus      (1)
                          51                                                 100
  AK005939       (1)   --------------------------------------------------
  hJ12 var1      (1)   --------------------------------------------------
  hJ12 var2      (1)   --------------------------------------------------
  hJ12 var3     (51)   GCCCTCATCTATAAAAATGGGATAACAGCTGGTGGTTCTAAGTGCGGCAG
  Consensus     (51)
                          101                                                150
  AK005939       (1)   --------------------------------------------------
  hJ12 var1      (1)   --------------------------------------------------
  hJ12 var2      (1)   --------------------------------------------------
  hJ12 var3    (101)   CTCCCGCAGGCAACAGGGTTTCACCATGTTGGCCAGGATGGTCTCGACCT
  Consensus    (101)
                          151                                                200
  AK005939       (1)   --------------------------------------------------
  hJ12 var1      (1)   --------------------------------------------------
  hJ12 var2      (1)   --------------------------------------------------
  hJ12 var3    (151)   TTTGACCTCGTGATCCGCCCGCCTCGGCCTCCCAAAGTGCTGGGATTACA
  Consensus    (151)
                          201                                                250
  AK005939       (1)   --------------------------------------------------
  hJ12 var1      (1)   --------------------------------------------------
  hJ12 var2      (1)   --------------------------------------------------
  hJ12 var3    (201)   GGCGTGAGCCACCGCACCCAGCCTTCTTTTTCTCTTGAGAGTGCCTTCTC
  Consensus    (201)
                          251                                                300
  AK005939       (1)   --------------------------------------------------
  hJ12 var1      (1)   --GGGGCAGGGGCCTCTCCAGGCGCTCTCACCTGCCCCG---AGGGAAAA
  hJ12 var2      (1)   ------------------GGCGCTCTCACCTGCCCCG---AGGGAAAA
  hJ12 var3    (251)   CATGTTCTAGATTAAATCATCATCTTCTC-CTTGTCCTGTTAATGGAAGC
  Consensus    (251)        G  C  G         TC  GGCGCTCTCACCTGCCCCG   AGGGAAAA
                          301                                                350
  AK005939       (1)   --------------------------------------------------
  hJ12 var1     (46)   GTCCCCCATCCGGATCAGACAGCCTGGCCCCAACCACCTGCGTTTTCTCT
  hJ12 var2     (28)   GTCCCCCATCCGGATCAGACAGCCTGGCCCCAACCACCTGCGTTTTCTCT
  hJ12 var3    (300)   ATGTCCCAGG-GCTCCACACGACTTCCACACCTCACAGTGC-TCATCTCT
  Consensus    (301)   GTCCCCCATCCGGATCAGACAGCCTGGCCCCAACCACCTGCGTTTTCTCT
```

Fig. 9-2

```
                     351                                                     400
    AK005939    (1)  ---GGCCTTCTCCTTATGCCTTCCCTG--TGTTCACTAGAGCCA----TC
    hJ12 var1  (96)  TCTGCCCTCATCTATAAAAATGGGATAACAGCTGG-TGGTTCTAAGTGCG
    hJ12 var2  (78)  TCTGCCCTCATCTATAAAAATGGGATAACAGCTGG-TGGTTCTAAGTGCG
    hJ12 var3 (348)  TACTGGCTTACAGTTTTATCTGCCACAATACCTTGATGGCAC------CC
    Consensus (351)  TCTGGCCTTATCTTTATAACTGGGATAACAGCTGG TGGTTCTAAGTGCG
                     401                                                     450
    AK005939   (42)  -CCCCTGCCTCCGGAATTCC------CA-----CAGAT------G---GA
    hJ12 var1 (145)  GCAGCTCCCGCAGGCATTCCTTCCTACACGCTTCAGATCCACACGTCCGA
    hJ12 var2 (127)  GCAGCTCCCGCAGGCAC---------------CAG-----------CAA
    hJ12 var3 (392)  ACATTTACATCTGTAGTTCCTTCCTACACGCTTCAGATCCACACGTCCGA
    Consensus (401)  GCAGCTCCCTCAGGCATTCCTTCCTACACGCTTCAGATCCACACGTCCGA
                     451                                                     500
    AK005939   (71)  TCGC----TCTGTGGCTTCT------------TAAAACTTCCC-TGCAGG
    hJ12 var1 (195)  CAGCCTACTGTGTGTCTTCAGCTGAGCATCCATAACACTTCCCATTCACT
    hJ12 var2 (150)  CAGC---------------------------------------------
    hJ12 var3 (442)  CAGCCTACTGTGTGTCTTCAGCTGAGCATCCATAACACTTCCCATTCACT
    Consensus (451)  CAGCCTACTGTGTGTCTTCAGCTGAGCATCCATAACACTTCCCATTCACT
                     501                                                     550
    AK005939  (104)  G---CACTGACCC--TCAGCCCTCTAAGTCACTTCTTCCC-CAGTGATT
    hJ12 var1 (245)  GTGTCAAAAGCTGAATCAGGCCGGGCACGTGGCTTGCACCTACAGTCGCA
    hJ12 var2 (154)  --------------------------------------------------
    hJ12 var3 (492)  GTGTCAAAAGCTGAATCAGGCCGGGCACGTGGCTTGCACCTACAGTCGCA
    Consensus (501)  GTGTCAAAAGCTGAATCAGGCCGGGCACGTGGCTTGCACCTACAGTCGCA
                     551                                                     600
    AK005939  (148)  GTACTTTTC-------AATCGGGCTTCAAACTTTCCTCTCATTAAATCAG
    hJ12 var1 (295)  GCACTTTGGGAGGCCAAGGCAGCCATGGCGAACACATCTGGCTCCAGAAG
    hJ12 var2 (154)  ----------------AGGCAGCCATGGCGAACACATCTGGCTCCAGAAG
    hJ12 var3 (542)  GCACTTTGGGAGGCCAAGGCAGCCATGGCGAACACATCTGGCTCCAGAAG
    Consensus (551)  GCACTTTGGGAGGCCAAGGCAGCCATGGCGAACACATCTGGCTCCAGAAG
                     601                                                     650
    AK005939  (191)  CAAGCACTTTCCAAGAAAAGAGAGATGCTCAAGATG-CCTTCCTGTGTGG
    hJ12 var1 (345)  CCCCCACTGAAGCTGGCCTTGCTCTCTCTCGCCATGGCCTCTCACTCAGG
    hJ12 var2 (188)  CCCCCACTGAAGCTGGCCTTGCTCTCTCTCGCCATGGCCTCTCACTCAGG
    hJ12 var3 (592)  CCCCCACTGAAGCTGGCCTTGCTCTCTCTCGCCATGGCCTCTCACTCAGG
    Consensus (601)  CCCCCACTGAAGCTGGCCTTGCTCTCTCTCGCCATGGCCTCTCACTCAGG
                     651                                                     700
    AK005939  (240)  AACAACGAAGCCTACCCTGGTGCTGCTTTGCTGTATAGGAACCTGGCTGG
    hJ12 var1 (395)  CCCCTCGACGTCTGTGCTCTTTCTGTTCTGCTGCCTGGGAGGCTGGCTGG
    hJ12 var2 (238)  CCCCTCGACGTCTGTGCTCTTTCTGTTCTGCTGCCTGGGAGGCTGGCTGG
    hJ12 var3 (642)  CCCCTCGACGTCTGTGCTCTTTCTGTTCTGCTGCCTGGGAGGCTGGCTGG
    Consensus (651)  CCCCTCGACGTCTGTGCTCTTTCTGTTCTGCTGCCTGGGAGGCTGGCTGG
                     701                                                     750
    AK005939  (290)  CCACCTGCAGCTTGTCCTTCGGTGCCCCAATATCGAAGGAAGACTTAAGA
    hJ12 var1 (445)  CCTCCCACACGTTGCCCGTCCGTTTACTACGACCAAGTGATGATGTACAG
    hJ12 var2 (288)  CCTCCCACACGTTGCCCGTCCGTTTACTACGACCAAGTGATGATGTACAG
    hJ12 var3 (692)  CCTCCCACACGTTGCCCGTCCGTTTACTACGACCAAGTGATGATGTACAG
    Consensus (701)  CCTCCCACACGTTGCCCGTCCGTTTACTACGACCAAGTGATGATGTACAG
```

Fig. 9-3

```
                         751                                              800
   AK005939   (340)  ACTACAATTGACCTCTTGAAACAAGAGTCTCAGGATCTTTATAAC-AACT
   hJ12 var1  (495)  AAAATAGTCGAGGAATTACAGTCCCTCTCGAAGATGCTTTTGAAAGATGT
   hJ12 var2  (338)  AAAATAGTCGAGGAATTACAGTCCCTCTCGAAGATGCTTTTGAAAGATGT
   hJ12 var3  (742)  AAAATAGTCGAGGAATTACAGTCCCTCTCGAAGATGCTTTTGAAAGATGT
  Consensus   (751)  AAAATAGTCGAGGAATTACAGTCCCTCTCGAAGATGCTTTTGAAAGATGT
                         801                                              850
   AK005939   (389)  ATAGCATAAAGCAGGCATCTGGGATGTCAGCAGACGAATCAATACA-GCT
   hJ12 var1  (545)  GGAGGAAGAGAAGGGCGTGCTCG-TGTCC-CAGA------ATTACACGCT
   hJ12 var2  (388)  GGAGGAAGAGAAGGGCGTGCTCG-TGTCC-CAGA------ATTACACGCT
   hJ12 var3  (792)  GGAGGAAGAGAAGGGCGTGCTCG-TGTCC-CAGA------ATTACACGCT
  Consensus   (801)  GGAGGAAGAGAAGGGCGTGCTCG TGTCC CAGA      ATTACACGCT
                         851                                              900
   AK005939   (438)  GCCGTGTTTCAGCCCTGGACCGGGAAGCATTAACCAACATCT------CGG
   hJ12 var1  (587)  GCCGTGTCTCAGCCCTGACGCCCAGCCGCCAAACAACATCCACAGCCCAG
   hJ12 var2  (430)  GCCGTGTCTCAGCCCTGACGCCCAGCCGCCAAACAACATCCACAGCCCAG
   hJ12 var3  (834)  GCCGTGTCTCAGCCCTGACGCCCAGCCGCCAAACAACATCCACAGCCCAG
  Consensus   (851)  GCCGTGTCTCAGCCCTGACGCCCAGCCGCCAAACAACATCCACAGCCCAG
                         901                                              950
   AK005939   (482)  TCATCATAGCACATCTGGAGAAAGTCAAAGTCTTGAGCGAGAACACAGTA
   hJ12 var1  (637)  CCATCCGGGCATATCTCAAGACAATCAGACAGCTA---GACAACAAATCT
   hJ12 var2  (480)  CCATCCGGGCATATCTCAAGACAATCAGACAGCTA---GACAACAAATCT
   hJ12 var3  (884)  CCATCCGGGCATATCTCAAGACAATCAGACAGCTA---GACAACAAATCT
  Consensus   (901)  CCATCCGGGCATATCTCAAGACAATCAGACAGCTA   GACAACAAATCT
                         951                                             1000
   AK005939   (532)  GATACTTCTTGGGTGATAAGATGGCTA-ACAAACATCAGCTGTTTCAACC
   hJ12 var1  (684)  GTTATTGATGAGATCATAGAGCACCTCGACAAAC-TCATATTTCAAGATG
   hJ12 var2  (527)  GTTATTGATGAGATCATAGAGCACCTCGACAAAC-TCATATTTCAAGATG
   hJ12 var3  (931)  GTTATTGATGAGATCATAGAGCACCTCGACAAAC-TCATATTTCAAGATG
  Consensus   (951)  GTTATTGATGAGATCATAGAGCACCTCGACAAAC TCATATTTCAAGATG
                        1001                                             1050
   AK005939   (581)  CAGTGAATTTAAACATTTCTGTGCCTGGAAATACTGATGAATCCTATGAT
   hJ12 var1  (733)  CACCAGAAACAAACATTTCTGTGCC----AACA-----GACACCCATGAA
   hJ12 var2  (576)  CACCAGAAACAAACATTTCTGTGCC----AACA-----GACACCCATGAA
   hJ12 var3  (980)  CACCAGAAACAAACATTTCTGTGCC----AACA-----GACACCCATGAA
  Consensus  (1001)  CACCAGAAACAAACATTTCTGTGCC    AACA     GACACCCATGAA
                        1051                                             1100
   AK005939   (631)  TGTAAAGTGTTCGTGCTTACGGTTTTAAAGCAGTTCTCAAACTGCATGGC
   hJ12 var1  (774)  TGTAAACGCTTCATCCTGACTATTTCTCAACAGTTTTCAGAGTGCATGG-
   hJ12 var2  (617)  TGTAAACGCTTCATCCTGACTATTTCTCAACAGTTTTCAGAGTGCATGG-
   hJ12 var3 (1021)  TGTAAACGCTTCATCCTGACTATTTCTCAACAGTTTTCAGAGTGCATGG-
  Consensus  (1051)  TGTAAACGCTTCATCCTGACTATTTCTCAACAGTTTTCAGAGTGCATGG
                        1101                                             1150
   AK005939   (681)  AGAACTGCAGGCTAAGGACAATACTACATGCTCAGTGATGGGCGGGGGGG
   hJ12 var1  (823)  ---ACCTCGCACTAAAATCATTG--ACCTCTGGAGCCCAACAGGCCACCA
   hJ12 var2  (666)  ---ACCTCGCACTAAAATCATTG--ACCTCTGGAGCCCAACAGGCCACCA
   hJ12 var3 (1070)  ---ACCTCGCACTAAAATCATTG--ACCTCTGGAGCCCAACAGGCCACCA
  Consensus  (1101)     ACCTCGCACTAAAATCATTG  ACCTCTGGAGCCCAACAGGCCACCA
                        1151                                             1200
   AK005939   (731)  GGTGCAGTGTCCTCAGCAGTGCCTGTCCTTCGAGGGCTGAGCTTGCAACC
   hJ12 var1  (868)  CTTAAAATAAA---------------------------------------
   hJ12 var2  (711)  CTTAAAATAAA---------------------------------------
   hJ12 var3 (1115)  CTTAAA--------------------------------------------
  Consensus  (1151)  CTTAAAATAAA
```

Fig. 9-4

```
                           1201                                              1250
    AK005939    (781)  CAGGACTTAACTCCAAAGGGACTGTGCGGTCATTACTAGTCATGTTATTT
    hJ12 var1   (879)  --------------------------------------------------
    hJ12 var2   (722)  --------------------------------------------------
    hJ12 var3  (1121)  --------------------------------------------------
    Consensus  (1201)
                           1251                                              1300
    AK005939    (831)  ATGTTTTTATTTTGTCCACTGAAATCTTGTTCTGCTACCCTGTAGGGACT
    hJ12 var1   (879)  --------------------------------------------------
    hJ12 var2   (722)  --------------------------------------------------
    hJ12 var3  (1121)  --------------------------------------------------
    Consensus  (1251)
                           1301                                              1350
    AK005939    (881)  GGAAGTGGCAGCTATATTTATTTATTTATGTACTGAGTTTGTTAACGCTC
    hJ12 var1   (879)  --------------------------------------------------
    hJ12 var2   (722)  --------------------------------------------------
    hJ12 var3  (1121)  --------------------------------------------------
    Consensus  (1301)
                           1351                                         1395
    AK005939    (931)  CATGGAGGAGCCTTCAGAGTCTATTTAATAAATTATATTGACATG
    hJ12 var1   (879)  ---------------------------------------------
    hJ12 var2   (722)  ---------------------------------------------
    hJ12 var3  (1121)  ---------------------------------------------
    Consensus  (1351)
```

TaqMan PCR confirmed J12 mRNA is highly induced in human Th2 cells by anti-CD3/CD28 stimulation Human J12 mRNA expression in normal tissues

Fig. 12

Alignment of human J12 var1, var2 partial protein sequences against the IL-4 and IL-13

```
QUERY         ----STSVLFLFCCLGGWLAS-HTLP-VR-  -LLRPSDDVQKIVEELQS
IL4_CERTO     MGLTSQLLPPLFFLLA  CAGNFAHGHNCH  IALR......EIIETLNS
IL4_MERUN     MGLSPQLAAVLLCLLV  CTGNYARRQDRE  AGLR......EIIHNLDQ
IL4_MOUSE     MGLNPQLVVILLFFLE  CTRSHIHG-CDK  NHLR......EIIGILNE
HSNC30_1      MALLLTTVIALTCLGG  FASPGPVPPST-  -ALR......ELIEELVN
JU0139        MGLTSQLIPALVCLLV  CTSHFVHGHKCD  ITLE......EIIKTPNI
IL4_RAT       MGLSPHLAVTLFCFLI  CTGNGIHG-CND  SPLR......EIINTLNQ
IL13_MOUSE    MALWVTAVLALACLGG  LAAPGPVPRSVSLPLTLK......ELIEELSN
IL4_MESAU     MGLRPQLAAILLCLLA  CTGNWTLG-CHH  GALK......EIIHILNQ
IL4_HORSE     MGLTSQLLPALVCLLA  CTS-FIQGCKYD  ITLQ......EIIKTLNL

QUERY         LSKMLLK------DVEE---------EKG-----VLVSQNYTL-----PC
IL4_CERTO     LTEQK.T-LCTKLTITDILAASKNTTEKETFCRAATVLRQFYSHHEKDTR
IL4_MERUN     VLKKE.T-PCTEMFVPDVLIATKNTTEKGLLCRATRVLRKFYFPREVTPC
IL4_MOUSE     VTGEG.T-PCTEMDVPNVLTATKNTTESELVCRASKVLRIFYLKHGKTPC
HSNC30_1      ITQNQKAPLCNGSMVWS-I----NLTAGM-YCAALESLINVSG-------
JU0139        LTSR-.KNSCMELPVADVFAAPKNATEKETFCRAGIELRRIYRS------
IL4_RAT       VTEKG.T-PCTEMFVPDVLTATRNTTENELICRASRVLRKFYFPRDVPPC
IL13_MOUSE    ITQDQ.TPLCNGSMVWS-V----DLAAGG-FCVALDSLTNISN-------
IL4_MESAU     VTEKG.T-PCTEMVVPDALSARKNSTEKDLICRASQGFRKFYFQHEVTLC
IL4_HORSE     TDGKG.KNSCMELTVADAFG-PKNTDGKE-ICRAAKVLQQYKRH------

QUERY         LSPDAQPPNNIHSPAIRAYLKTIRQLDNKSVIDEIIEHLDKLIFQDAPET
IL4_CERTO     CLGASA.................QQFHRHKQLIRFLKRLDRNLWGLAGLN
IL4_MERUN     LK........................NNSGVLSILRKLCRSISTLHPQE
IL4_MOUSE     LK........................KNSSVLMELQRLFRAFRCLDSSI
HSNC30_1      --........................-CSAIEKTQRMLSGFCPHKVSAG
JU0139        --........................-HMCLNKFLGGLDRNLSSLASKT
IL4_RAT       LK........................NKSGVLGELRKLCRGVSGLNSLR
IL13_MOUSE    --........................-CNAIYRTQRILHGLCNRKAPTT
IL4_MESAU     LK........................NNSRVLKDLKKLYRGISSLFPQK
IL4_HORSE     --........................DRSLIKECLSGLDRN-KGMANGT

QUERY         --NISVPTDT-HECKRFI---LTISQQ-FSECMD...
IL4_CERTO     SCPVKEASQS--TLEDFLERLKTIMREKYSKCSS...
IL4_MERUN     SCSVSTPTLT--TLNDFLGRLRGIMQMKNWQG--...
IL4_MOUSE     SCTMNESKST--SLKDFLESLKSIMQMDYS----...
HSNC30_1      QFSSLHVRDTKIEVAQFVKDLLLHLKKLFREGRFN
JU0139        -CSVNEAKTSTSTLRDLLERLKTIMREKYSKC--...
IL4_RAT       SCTVNESTLT--TLKDFLESLKSILRGKYLQSCTSMS
IL13_MOUSE    ---VSSLPDTKIEVAHFITKLLSYTKQLFRHGPF...
IL4_MESAU     SCNVNESTYT--TLKDFLESLRRIMQKKYWQCGSSTF
IL4_HORSE     CCTVNEAKKS--TL-DFLERLKTIMREKYSKCS-...
```

Fig. 13-1

Mouse J12 vs AY509149 (IL31) cDNA sequence

```
                        1                                                50
Mouse J12       (1)     AGAACGCAAGGACAAGGGCAGGCCCTGGAGCACAGATGCCTTCTCCTTAT
AY509149        (1)     -------------------------------------------------
Consensus       (1)
                        51                                               100
Mouse J12      (51)     TTCCCTGTGTTCACTAGAGCCATCCCCCTGCCTCCGGAATTCCCACA
AY509149        (1)     --GCC------------------------------------------
Consensus      (51)
                        101                                              150
Mouse J12     (101)     GATGGATCGCTCTGTGGCTTCTTAAAACTTCCCTGCAGGGCACTGACCCT
AY509149        (1)     --------------------------------------------------
Consensus     (101)
                        151                                              200
Mouse J12     (151)     CAGCCCCTCTAAGTCACTTCTTCCCCAGTGATTGTACTTTTCAATCGGGC
AY509149        (1)     --------------------------------------------------
Consensus     (151)
                        201                                              250
Mouse J12     (201)     TTCAAACTTTCCTCTCATTAAATCAGCAAGCACTTTCCAAGAAAAGAGAG
AY509149        (1)     --------------------------------------------------
Consensus     (201)
                        251                                              300
Mouse J12     (251)     ATGCTCAAGATGCCTTCCTGTGTGCCCTGCTTTCCCCAGGCCGAGCCGAG
AY509149        (1)     --------------------------------------------------
Consensus     (251)
                        301                                              350
Mouse J12     (301)     GCTGGCAACCTTTTGAAAATGTTTTCTGGAGAAAAGCTGAGCAATGGTTT
AY509149        (1)     --------------------------------------------------
Consensus     (301)
                        351                                              400
Mouse J12     (351)     TGCCATGGGCGGGCCTTTGATCTGCTTCCTCATGACAACCCTTTATATAT
AY509149        (1)     --------------------------------------------------
Consensus     (351)
                        401                                              450
Mouse J12     (401)     TGCCTGGTGGCCATGGCGAACACACCAGGCTCCAGAGACCACAGGCAAAG
AY509149        (1)     --------------------------GGCTCCAGAGACCACAGGCAAAG
Consensus     (401)                               GGCTCCAGAGACCACAGGCAAAG
                        451                                              500
Mouse J12     (451)     CGGGCCTTCCTCACTCTCTTACCGTCGCCATGATCTTCCACACACGGAACA
AY509149       (24)     CGGGCCTTCCTCACTCTCTTACCGTCGCCATGATCTTCCACACACGGAACA
Consensus     (451)     CGGGCCTTCCTCACTCTCTTACCGTCGCCATGATCTTCCACACACGGAACA
                        501                                              550
Mouse J12     (501)     ACGAAGCCTACCCTGGTGCTGCTTTGCTGTATAGGAACCTGGCTGGCCAC
AY509149       (74)     ACGAAGCCTACCCTGGTGCTGCTTTGCTGTATAGGAACCTGGCTGGCCAC
Consensus     (501)     ACGAAGCCTACCCTGGTGCTGCTTTGCTGTATAGGAACCTGGCTGGCCAC
                        551                                              600
Mouse J12     (551)     CTGCAGCTTGTCCTTCGGTGCCCCAATATCGAAGGAAGACTTAAGAACTA
AY509149      (124)     CTGCAGCTTGTCCTTCGGTGCCCCAATATCGAAGGAAGACTTAAGAACTA
Consensus     (551)     CTGCAGCTTGTCCTTCGGTGCCCCAATATCGAAGGAAGACTTAAGAACTA
                        601                                              650
Mouse J12     (601)     CAATTGACCTCTTGAAACAAGAGTCTCAGGATCTTTATAACAACTATAGC
AY509149      (174)     CAATTGACCTCTTGAAACAAGAGTCTCAGGATCTTTATAACAACTATAGC
Consensus     (601)     CAATTGACCTCTTGAAACAAGAGTCTCAGGATCTTTATAACAACTATAGC
```

Fig. 13-2

```
                        651                                              700
Mouse J12    (651)  ATAAAGCAGGCATCTGGGATGTCAGCAGACGAATCAATACAGCTGCCGTG
AY509149     (224)  ATAAAGCAGGCATCTGGGATGTCAGCAGACGAATCAATACAGCTGCCGTG
Consensus    (651)  ATAAAGCAGGCATCTGGGATGTCAGCAGACGAATCAATACAGCTGCCGTG
                        701                                              750
Mouse J12    (701)  TTTCAGCCTGGACCGGGAAGCATTAACCAACATCTCGGTCATCATAGCAC
AY509149     (274)  TTTCAGCCTGGACCGGGAAGCATTAACCAACATCTCGGTCATCATAGCAC
Consensus    (701)  TTTCAGCCTGGACCGGGAAGCATTAACCAACATCTCGGTCATCATAGCAC
                        751                                              800
Mouse J12    (751)  ATCTGGAGAAAGTCAAAGTGTTGAGCGAGAACACAGTAGATACTTCTTGG
AY509149     (324)  ATCTGGAGAAAGTCAAAGTGTTGAGCGAGAACACAGTAGATACTTCTTGG
Consensus    (751)  ATCTGGAGAAAGTCAAAGTGTTGAGCGAGAACACAGTAGATACTTCTTGG
                        801                                              850
Mouse J12    (801)  GTGATAAGATGGCTAACAAACATCAGCTGTTTCAACCCACTGAATTTAAA
AY509149     (374)  GTGATAAGATGGCTAACAAACATCAGCTGTTTCAACCCACTGAATTTAAA
Consensus    (801)  GTGATAAGATGGCTAACAAACATCAGCTGTTTCAACCCACTGAATTTAAA
                        851                                              900
Mouse J12    (851)  CATTTCTGTGCCTGGAAATACTGATGAATCCTATGATTGTAAAGTGTTCG
AY509149     (424)  CATTTCTGTGCCTGGAAATACTGATGAATCCTATGATTGTAAAGTGTTCG
Consensus    (851)  CATTTCTGTGCCTGGAAATACTGATGAATCCTATGATTGTAAAGTGTTCG
                        901                                              950
Mouse J12    (901)  TGCTTACGGTTTTAAAGCAGTTCTCAAACTGCATGGCAGAACTGCAGGCT
AY509149     (474)  TGCTTACGGTTTTAAAGCAGTTCTCAAACTGCATGGCAGAACTGCAGGCT
Consensus    (901)  TGCTTACGGTTTTAAAGCAGTTCTCAAACTGCATGGCAGAACTGCAGGCT
                        951                                             1000
Mouse J12    (951)  AAGGACAATACTACATGCTGAGTGATGGGGGGGGGGGGTGCAGTGTCCT
AY509149     (524)  AAGGACAATACTACATGCTGAGTGATGGGGGGGGGG---TGCAGTGTCCT
Consensus    (951)  AAGGACAATACTACATGCTGAGTGATGGGGGGGGGG    TGCAGTGTCCT
                       1001                                             1050
Mouse J12   (1001)  CAGCAGTGCCTGTCCTTCGAGGGCTGAGCTTGCAACCCAGGACTTAACTC
AY509149     (571)  CAGCAGTGCCTGTCCTTCGAGGGCTGAGCTTGCAACCCAGGACTTAACTC
Consensus   (1001)  CAGCAGTGCCTGTCCTTCGAGGGCTGAGCTTGCAACCCAGGACTTAACTC
                       1051                                             1100
Mouse J12   (1051)  CAAAGGGACTGTGCGGTCATTACTAGTCATGTTATTTATGTTTTTATTTT
AY509149     (621)  CAAAGGGACTGTGCGGTCATTACTAGTCAT--------------------
Consensus   (1051)  CAAAGGGACTGTGCGGTCATTACTAGTCAT
                       1101                                             1150
Mouse J12   (1101)  GTCCACTGAAATCTTGTTCTGCTACCCTGTAGGGACTGGAAGTGGCAGCT
AY509149     (651)  --------------------------------------------------
Consensus   (1101)
                       1151                                             1200
Mouse J12   (1151)  ATATTTATTTATTTATGTACTGAGTTTGTTAACGCTCCATGGAGGAGCCT
AY509149     (651)  --------------------------------------------------
Consensus   (1151)
                       1201                                             1249
Mouse J12   (1201)  TCAGAGTCTATTTAATAAATTATATTGACATGAAAAAAAAAAAAAAAAA
AY509149     (651)  -------------------------------------------------
Consensus   (1201)
```

Fig. 14

Human J12 var1 (Human J12-Var1) vs AY499343 (IL31) amino acid sequences

```
                    1                                                  50
Human J12-1    (1)  GRGLSRRSHLPRGKSPPSGSDSLAPTTCVFSSALIYKNGITAGGSKCGSS
   AY499343    (1)  --------------------------------------------------
  Consensus    (1)
                    51                                                100
Human J12-1   (51)  RRHSFLHASDPHVRQPTVCLQLSIHNTSHSLCQKLNQAGHVACTYSRSTL
   AY499343    (1)  --------------------------------------------------
  Consensus   (51)
                    101                                               150
Human J12-1  (101)  GGQGSHGEHIWLQKPPLKLALLSLAMASHSGPSTSVLFLFCCLGGWLASH
   AY499343    (1)  ------------------------MASHSGPSTSVLFLFCCLGGWLASH
  Consensus  (101)                          MASHSGPSTSVLFLFCCLGGWLASH
                    151                                               200
Human J12-1  (151)  TLPVRLLRPSDDVQKIVEELQSLSKMLLKDVEEEKGVLVSQNYTLPCLSP
   AY499343   (26)  TLPVRLLRPSDDVQKIVEELQSLSKMLLKDVEEEKGVLVSQNYTLPCLSP
  Consensus  (151)  TLPVRLLRPSDDVQKIVEELQSLSKMLLKDVEEEKGVLVSQNYTLPCLSP
                    201                                               250
Human J12-1  (201)  DAQPPNNIHSPAIRAYLKTIRQLDNKSVIDEIIEHLDKLIFQDAPETNIS
   AY499343   (76)  DAQPPNNIHSPAIRAYLKTIRQLDNKSVIDEIIEHLDKLIFQDAPETNIS
  Consensus  (201)  DAQPPNNIHSPAIRAYLKTIRQLDNKSVIDEIIEHLDKLIFQDAPETNIS
                    251                              289
Human J12-1  (251)  VPTDTHECKRFILTISQQFSECMDLALKSLTSGAQQATT
   AY499343  (126)  VPTDTHECKRFILTISQQFSECMDLALKSLTSGAQQATT
  Consensus  (251)  VPTDTHECKRFILTISQQFSECMDLALKSLTSGAQQATT
```

Fig. 15

Human J12 var2 (Human J12Var2) vs AY499343 (IL31) amino acid sequences

```
                    1                                                50
Human J12-2    (1)  MASHSGPSTSVLFLFCCLGGWLASHTLPVRLLRPSDDVQKIVEELQSLSK
   AY499343    (1)  MASHSGPSTSVLFLFCCLGGWLASHTLPVRLLRPSDDVQKIVEELQSLSK
  Consensus    (1)  MASHSGPSTSVLFLFCCLGGWLASHTLPVRLLRPSDDVQKIVEELQSLSK
                    51                                              100
Human J12-2   (51)  MLLKDVEEEKGVLVSQNYTLPCLSPDAQPPNNIHSPAIRAYLKTIRQLDN
   AY499343   (51)  MLLKDVEEEKGVLVSQNYTLPCLSPDAQPPNNIHSPAIRAYLKTIRQLDN
  Consensus   (51)  MLLKDVEEEKGVLVSQNYTLPCLSPDAQPPNNIHSPAIRAYLKTIRQLDN
                    101                                             150
Human J12-2  (101)  KSVIDEIIEHLDKLIFQDAPETNISVPTDTHECKRFILTISQQFSECMDL
   AY499343  (101)  KSVIDEIIEHLDKLIFQDAPETNISVPTDTHECKRFILTISQQFSECMDL
  Consensus  (101)  KSVIDEIIEHLDKLIFQDAPETNISVPTDTHECKRFILTISQQFSECMDL
                    151       164
Human J12-2  (151)  ALKSLTSGAQQATT
   AY499343  (151)  ALKSLTSGAQQATT
  Consensus  (151)  ALKSLTSGAQQATT
```

Fig. 16

Human J12 var2 (Human J12Var3) vs AY499343 (IL31) amino acid sequences

```
                 1                                                50
Human J12-3   (1) MEACPRAPHDFHTSHCSSLTGLQFYLPQYLDGTHIYICSSFLHASDPHVR
   AY499343   (1) --------------------------------------------------
  Consensus   (1)
                 51                                               100
Human J12-3  (51) QPTVCLQLSIHNTSHSLCQKLNQAGHVACTYSRSTLGGQGSHGEHIWLQK
   AY499343   (1) --------------------------------------------------
  Consensus  (51)
                 101                                              150
Human J12-3 (101) PPLKLALLSLAMASHSGPSTSVLFLFCCLGGWLASHTLPVRLLRPSDDVQ
   AY499343   (1) -----------MASHSGPSTSVLFLFCCLGGWLASHTLPVRLLRPSDDVQ
  Consensus (101)            MASHSGPSTSVLFLFCCLGGWLASHTLPVRLLRPSDDVQ
                 151                                              200
Human J12-3 (151) KIVEELQSLSKMLLKDVEEEKGVLVSQNYTLPCLSPDAQPPNNIHSPAIR
   AY499343  (40) KIVEELQSLSKMLLKDVEEEKGVLVSQNYTLPCLSPDAQPPNNIHSPAIR
  Consensus (151) KIVEELQSLSKMLLKDVEEEKGVLVSQNYTLPCLSPDAQPPNNIHSPAIR
                 201                                              250
Human J12-3 (201) AYLKTIRQLDNKSVIDEIIEHLDKLIFQDAPETNISVPTDTHECKRFILT
   AY499343  (90) AYLKTIRQLDNKSVIDEIIEHLDKLIFQDAPETNISVPTDTHECKRFILT
  Consensus (201) AYLKTIRQLDNKSVIDEIIEHLDKLIFQDAPETNISVPTDTHECKRFILT
                 251                    275
Human J12-3 (251) ISQQFSECMDLALKSLTSGAQQATT
   AY499343 (140) ISQQFSECMDLALKSLTSGAQQATT
  Consensus (251) ISQQFSECMDLALKSLTSGAQQATT
```

T CELL PROTEINS AND NUCLEOTIDES ENCODING THE SAME

RELATED APPLICATIONS

This application is a divisional of U.S. patent application Ser. No. 11/262,688 filed Oct. 31, 2005 and claims the benefit of U.S. Provisional Application No. 60/624,605 filed Nov. 3, 2004 the contents of which are incorporated herein in their entirety.

FIELD OF THE INVENTION

The invention relates to the field of inflammatory and autoimmune diseases and in particular to a protein designated J12 that is preferentially expressed in Th2 cells.

BACKGROUND INFORMATION

Proteins such as cytokines produced by T helper 1 (Th1) and T helper 2 cells (Th2) cells are thought to play critical roles in autoimmune and inflammatory diseases and it is thought that these diseases can be treated using methods to alter the activities of these proteins. Consequently, genes that are expressed in (Th1) and (Th2) cells are of interest.

Naïve CD4+ T cells can differentiate to Th1 and Th2 cells. Th1 cells are characterized for their production of IFN-γ but not IL-4 while Th2 cells produce IL-4 but not IFN-γ. IFN-γ and IL-4 are two major cytokines involved in autoimmunity and inflammation. After the engagement of TCR-peptide-MHC class II complex, naïve CD4+ T cells expend and develop to Th1 cells when IL-12 but not IL-4 is present; cells develop to Th2 cells when the environment has IL-4 but not IL-12.

CD4+ Th1 play critical roles in cell-mediated immune response while Th2 cells are involve in humoral immunity. However, over activation of CD4+ Th1 and Th2 cells may induce autoimmune and inflammatory diseases. For example, Th2, and also Th1, responses are involved in asthma. Th1 or Th2 responses might be the cause of different type of IBD and myocarditis. Type I diabetes and arthritis may be caused by Th1 response. In order to inhibit the Th1 or Th2 response, it is necessary to discover Th1 or Th2-specific genes which may be involved in their proliferation, differentiation and/or or cytokine production.

The cytokines and surface molecules of Th1/Th2 are involved in the autoimmune and inflammatory diseases. IFNγ, TNFα and IL-2 are mainly produced by Th1 cells, while IL-4, IL-5 and IL-13 are mainly produced by Th2 cells. IFNγ, TNFα and IL-2 all play important roles in the Th1-mediated diseases, such as IBD, MS, EAE, diabetes and arthritis. IL-4 is thought to play a role in asthma. Meanwhile, B7s and B7 receptors play critical roles in the stimulation or inhibition of T cell activation. B7.1 (CD80) and B7.2 (CD86) expressed on antigen presenting cells could stimulate either CD28 or CTLA-4 (CD152) expressed on T cells. Once B7-CD28 ligation occurs, T cells receive positive signals and the cells will be activated with the combination of TCR signals. However, when B7 stimulates CTLA-4, the T cell activation will be inhibited by the CTLA-4 signal. Programmed death receptor 1 (PD-1) is another inhibitory surface molecule. PD-1 deficient mice developed autoimmunity. Finally, a new inhibitory receptor called B and T lymphocyte attenuator (BTLA), initially discovered by Jianfei Yang and Ken Murphy, was recently published in *Nature Immunology* (2003) 4: 670-679. Increased EAE susceptibility in BTLA-deficient mice was found.

BRIEF SUMMARY OF THE INVENTION

The present invention is based on the discovery of novel mouse and human DNA sequences designated herein as J12 and variants and fragments thereof that are differentially expressed in CD4+ Th2 cells. The nucleic acid and polypeptides sequences described herein can be used in the diagnosis, characterization and or treatment of autoimmune and inflammatory disease diseases. present invention also provides polypeptides and fragments thereof that are encoded by said cDNA sequences. The present invention also provides for antibodies directed to the J12 polypeptides and to expression vectors comprised of J12 DNA sequences and cultured cells that contain the J12 expression vectors.

One embodiment of the invention is a polypeptide comprised of SEQ ID NO: 2 which is the mouse J12 protein sequence. Other embodiments of the invention are the polypeptides of SEQ ID. No's 6-8 which correspond to the polypeptides of three human J12 variants designated Var1, Var2 and Var3.

The invention also encompasses derivatives of the J12 polypeptides. A preferred derivative will have at least 90% polynucleotide identity to the polynucleotide encoding the polypeptides consisting of amino acid sequence of SEQ ID NO's 2 and 6-8. The polynucleotide variants described above can encode polypeptides which contains at least one functional or structural characteristic of J12.

It will be appreciated by those skilled in the art that a multitude of polynucleotide sequences encoding mouse and human J12 sequence, some bearing minimal homology to the polynucleotide sequences of any known and naturally occurring gene may be produced due to the degeneracy of the genetic code. Thus, the present invention also contemplates variations of polynucleotide sequence that could be made by selecting combinations based on alternative codon choices. These combinations are made in accordance with the standard triplet genetic code as applied to the polynucleotide sequence of naturally mouse and human J12.

The invention also encompasses production of DNA sequences which encode human and mouse J12 and J12 derivatives, or fragments thereof, entirely by chemical synthesis. Synthetic sequences may be inserted into expression vectors and host cell systems using reagents that are well known in the art. Moreover synthetic chemistry may be used to introduce mutations into a sequence encoding J12 or any fragment thereof.

Also encompassed by the invention are polynucleotide sequences that are capable of hybridizing to the claimed polynucleotide sequences, and, in particular, to those shown in SEQ ID NO: 1, (mouse J12 cDNA), and SEQ ID. No's 3-5 (human J12 variants) as well as fragments thereof under various conditions of stringency. (See, e.g., Wahl, G. M. and S. L. Berger (1987) Methods Enzymol. 152:399-407; and Kimmel, A. R. (1987) Methods Enzymol. 152:507-511).

Also encompassed by the invention are isolated nucleic acid sequence comprising a sequence at least 80% identical to Var1 and Var3 (SEQ ID No. 3 and SEQ ID No. 5). More preferably the invention encompasses isolated nucleic acid sequences comprising a sequence at least 95% identical to Var1 and Var3.

J12 encoding nucleotide sequences possessing non-naturally occurring codons may also be used. For example, codons preferred by a prokaryotic host can be used to increase protein expression or to produce an RNA transcript having desirable properties, such as a half-life which is longer than that of a transcript generated from the naturally occurring sequence.

The nucleotide sequences of the present invention can be altered using methods generally known in the art in order to alter J12 encoding sequences by cloning, processing, and/or expression of the gene product. Recombinant DNA techniques and synthetic oligonucleotides may be used to alter the nucleotide sequences.

In another embodiment of the invention, the polynucleotides encoding J12, or derivatives thereof, may be used for therapeutic purposes. In one aspect, the complement of the polynucleotide encoding J12 may be used in situations in which it would be desirable to block the transcription of the mRNA. In particular, cells may be transformed with sequences complementary to polynucleotides encoding J12. Thus, complementary molecules or fragments may be used to modulate J12 activity. Such technology is now well known in the art, and sense or antisense, or siRNA, RNA interference oligonucleotides or larger fragments can be designed from various locations along the coding or control regions of sequences encoding J12. RNA interference oligos and antisense oligos could be designed using the sequence of J12 splice variant to specifically inhibit the function of the J12 isoform. RNA interference is a process employing sequence-specific post-transcriptional gene silencing or gene knockdown by providing a double-stranded RNA (dsRNA) that is homologous in sequence to the targeted gene. Small interfering RNAs (siRNAs) can be synthesized in vitro or generated by ribonuclease III cleavage from longer dsRNA and are the mediators of sequence-specific mRNA degradation. SiRNA can be designed according to the technique described by Tuschl, described as follows. Elbashir, S M et al, Nature, 2001, 411, 494-498.

The protein encoded by this novel J12 variant could be selected for use in protein therapeutics. For example, monoclonal antibodies against J12 splice variant polypeptides can be produced. Methods for producing monoclonal antibodies against isolated proteins and their administration to cells are known in the art. Am J Gastroenterol. 2002, 97:2962-72. Monoclonal antibodies directed against the J12 splice variant polypeptides of the invention can be administered to cells to inhibit the function of the protein, and therefore to treat autoimmune, inflammatory and other related diseases.

It is also contemplated that the J12 splice variant of the present invention can be used in screening assays and ultra high throughput assays to identify small molecule inhibitors of the J12 splice variant polypeptides. Small molecule inhibitors could block the binding of this J12 variant to its cell surface receptor. Small molecule inhibitors can be used to block cytokine-receptor interactions. The mechanism could be through occupying protein-protein interacting site on J12, or cause conformation changes of J12

In another embodiment of the invention, natural, modified, or recombinant nucleic acid sequences encoding J12 may be ligated to a heterologous sequence to encode a fusion protein. For example peptide libraries can be screened for inhibitors of J12 activity. It may also be useful to encode a chimeric J12 protein that can be recognized by antibodies that are commercially available. Fusion proteins may also be made to contain cleavage sites between the J12 encoding sequence and other heterologous protein sequence, so that J12 may be cleaved and purified away from the heterologous moiety.

The present invention provides for isolated nucleic acids comprising sequences that encode mouse J12 polypeptides and human J12 variants taught herein.

The present invention also provides isolated nucleic acids comprising sequences that hybridize under highly stringent conditions to hybridization probes of the J12 mouse and human J12 variant sequences.

The present invention also provides isolated nucleic acids comprising sequences having at least 80% identity to the mouse J12 and human J12 variants taught herein.

The present invention also provides isolated nucleic acids comprising sequences that encodes polypeptides comprising the amino acid sequence of mouse and human J12 variants as taught herein that are at least 8 residues in length.

The present invention also provides purified immunogenic polypeptides, the amino acid sequence of which comprises at least ten consecutive residues of mouse and human J12 sequences as taught herein.

Another embodiment of the invention relates to a method of identifying a compound that inhibits the binding of J12 to its natural binding partner, the method comprising,
   a) providing a J12 polypeptide comprising selected from SEQ ID No. 2, 6-8 or a combination thereof
   b) contacting the polypeptide with its natural binding partner and a test compound
   c) determining whether binding of the binding partner to the polypeptide is decreases in the presence of the test compound, a decrease in said binding being an indication that the test compound inhibits the binding of J12 to its binding partner.

It is contemplated that a recombinant receptor of J12 could used to inhibit J12 binding to its natural receptor.

BRIEF DESCRIPTION OF THE FIGURES

FIG. 1 shows an alignment of mouse J12 cDNA sequence (SEQ ID No. 1) with EST AK005939 (SEQ ID No. 23).

FIG. 6A shows the Human J12 variant 1 protein sequence (SEQ ID No. 6).

FIG. 6B shows the Human J12 variant 2 protein sequence (SEQ ID No. 7).

FIG. 6C shows the Human J12 variant 3 protein sequence (SEQ ID No. 8).

FIG. 7*a-b* shows Human J12 splicing variant gene structure (SEQ ID Nos. 3-5).

FIG. 8 shows SMART sequence analysis of human J12 var1 (SEQ ID No. 6), human J12 var2 (SEQ ID No. 7) and human J12 var3 (SEQ ID No. 8) protein sequences.

FIG. 9 shows an alignment of the EST AK005939 (SEQ ID No. 23) and human J12 variant 1 (SEQ ID No. 3), human J12 variant 2 (SEQ ID No. 4) and human J12 variant 3 (SEQ ID No. 5) DNA.

FIG. 12 shows the alignment of the human J12, Var1, Var2 partial protein sequences against rat IL4 (SEQ ID No. 24), mouse IL4 (SEQ ID No. 25), mesau IL4 (SEQ ID No. 26), merun IL4 (SEQ ID No. 27), certo IL4 (SEQ ID No. 28), horse IL4 (SEQ ID No. 29), mouse IL13 (SEQ ID No. 30), JU0139 (SEQ ID No. 31) and HSNC30 1 (SEQ ID No. 32).

FIG. 13 shows the alignment of mouse J12 (SEQ ID No. 1) vs AY509149 (IL31) (SEQ ID No. 33) cDNA sequences.

FIG. 14 shows human J12 var1 (Human J12-1) (SEQ ID No. 6) vs AY499343 (IL31) (SEQ ID No. 34) amino acid sequences.

FIG. 15 shows human J12 var2 (Human J12-2) (SEQ ID No. 7) vs AY499343 (IL31) (SEQ ID No. 34) amino acid sequences.

FIG. 16 shows human J12 var3 (Human J12-2) (SEQ ID No. 8) vs AY499343 (IL31) (SEQ ID No. 34) amino acid sequences.

BRIEF DESCRIPTION OF THE SEQUENCES

Figure 2:
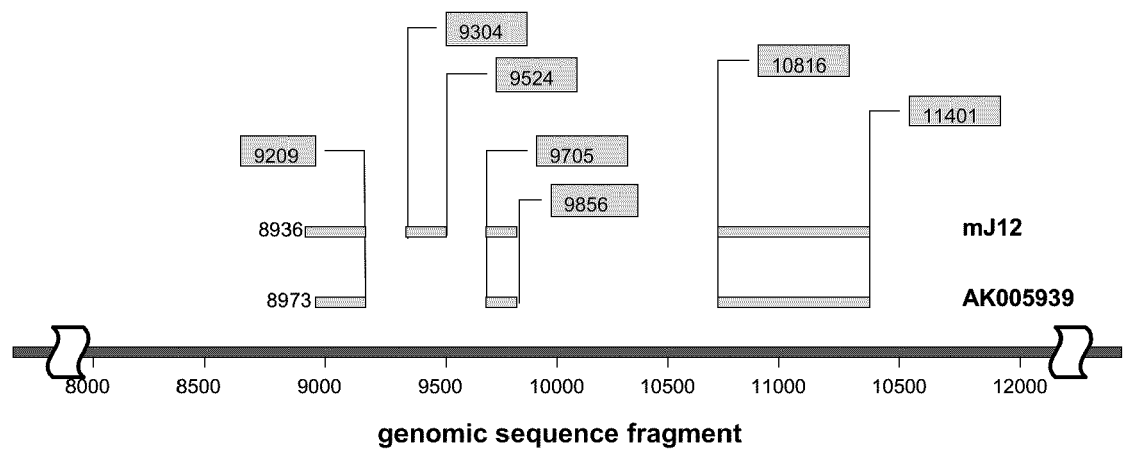
FIG. 2A shows the mouse J12 protein sequence (SEQ ID No. 2) and cleavage site.
FIG. 2B shows the mouse J12 gene structure (SEQ ID No. 1) vs. AK005939 (SEQ ID No. 23).
FIG. 2C shows the mouse J12 gene genomic structure (SEQ ID No. 1).

SEQ ID No. 1 is the mouse J12 cDNA sequence
SEQ ID No. 2 is the mouse J12 protein sequence
SEQ ID No. 3 is human J12 variant 1 DNA full length
SEQ ID No. 4 is human J12 variant 2 DNA full length
SEQ ID No. 5 is human J12 variant 3 DNA full length
SEQ ID No. 6 is human J12 variant 1 protein
SEQ ID No. 7 is human J12 variant 2 protein
SEQ ID No. 8 is human J12 variant 3 protein
SEQ ID No. 9 is J12 PCR forward primer
SEQ ID No. 10 is J12 PCR reverse primer
SEQ ID No. 11 is TaqMan® FAM-MGB probe:
SEQ ID No. 12 is human J12 forward TaqMan primer
SEQ ID No. 13 is human J12 reverse Taqman primer
SEQ ID No. 14 is Human J12 TaqMan® FAM-MGB probe
SEQ ID No. 15 is mouse J12 cDNA
SEQ ID No. 16 is human J12 Var3 DNA fragment
SEQ ID No. 17 is human J12 Var3 DNA fragment
SEQ ID No. 18 is human J12 Var1 DNA fragment
SEQ ID No. 19 is human J12 var2 DNA fragment
SEQ ID No. 20 is mouse J12 '3 cDNA
SEQ ID No. 21 is human J12 polypeptide 1-125 of var1
SEQ ID No. 22 is human J12 Var3 polypeptide 1-111 or var3
SEQ ID No. 23 is the mouse EST AK005939 cDNA sequence
SEQ ID No. 24 is the rat IL4 amino acid sequence
SEQ ID No. 25 is the mouse IL4 amino acid sequence
SEQ ID No. 26 is the mesau IL4 amino acid sequence
SEQ ID No. 27 is the merun IL4 amino acid sequence
SEQ ID No. 28 is the certo IL4 amino acid sequence
SEQ ID No. 29 is the horse IL4 amino acid sequence
SEQ ID No. 30 is the mouse IL13 amino acid sequence
SEQ ID No. 31 is the JU0139 amino acid sequence
SEQ ID No. 32 is the HSNC30 1 amino acid sequence
SEQ ID No. 33 is the mouse AY509149 (IL31) cDNA sequence
SEQ ID No. 34 is the human AY499343 (IL31) amino acid sequence

DETAILED DESCRIPTION OF THE INVENTION

Definitions

Unless defined otherwise, the scientific and technological terms and nomenclature used herein have the same meaning as commonly understood by a person of ordinary skill in the art to which this invention pertains.

In accordance with the present invention there may be employed conventional molecular biology, microbiology, and recombinant DNA techniques well known in the art and are described by Sambrook, J., Fritsch, E. F. and Maniatis, T., Molecular Cloning: A Laboratory Manual, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., Experiments with Gene Fusions, Cold Spring Harbor Laboratory Cold Press Spring Harbor, N.Y. (1984); and by Ausubel, F. M. et al., Current Protocols in Molecular Biology, published by Greene Publishing Assoc. and Wiley-Interscience (1987). "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells and Enzymes" [IRL Press, (1986)]; B. Perbal, "A Practical Guide To Molecular Cloning" (1984) and Current Protocols in Molecular Biology, John Wiley and Sons, July, 2002. Therefore, if appearing herein, the following terms shall have the definitions set out below.

The use of the singular forms of the terms "a", "an," and "the" include plural reference unless the context clearly indicates otherwise.

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission (Biochemistry, 1972, 11:1726-1732).

As used herein the term "polypeptide" is used interchangeably with amino acid residue sequences or protein and refers to polymers of amino acids of any length. These terms also include proteins that are post-translationally modified through reactions that include, but are not limited to, glycosylation, acetylation, phosphorylation or protein processing. Modifications and changes, for example fusions to other proteins, amino acid sequence substitutions, deletions or insertions, can be made in the structure of a polypeptide while the molecule maintains its biological functional activity. For example, certain amino acid sequence substitutions can be made in a polypeptide or its underlying nucleic acid coding sequence and a protein can be obtained with like properties.

As used herein, the term "cDNA" in the context of this invention refers to deoxyribonucleic acids produced by reverse transcription and typically second-strand synthesis of mRNA or other RNA produced by a gene. If double-stranded, a cDNA molecule has both a coding or sense and a non-coding or antisense strand.

The terms "fragment" of the present invention refer herein to proteins or nucleic acid molecules which can be isolated/purified, synthesized chemically or produced through recombinant DNA technology. All these methods are well known in the art. As exemplified herein below, the nucleotide sequences and polypeptides used in the present invention can be modified, for example by in vitro mutagenesis.

As used herein the term "encoding" refers to the inherent property of specific sequences of nucleotides in a nucleic acid, to serve as templates for synthesis of other molecules having a defined sequence of nucleotides (i.e. rRNA, tRNA, other RNA molecules) or amino acids and the biological properties resulting therefrom. Thus a gene encodes a protein, if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for the transcription, of a gene or cDNA can be referred to as encoding the protein or other product of that gene or cDNA. A nucleic acid that encodes a protein includes any nucleic acids that have different nucleotide sequences but encode the same amino acid sequence of the protein due to the degeneracy of the genetic code. Nucleic acids and nucleotide sequences that encode proteins may include introns.

The terminology "expression vector" defines a vector or vehicle as described above but designed to enable the expression of an inserted sequence following transformation into a host. The cloned gene (inserted sequence) is usually placed under the operation of control element sequences such as promoter sequences. Such expression control sequences will vary depending on whether the vector is designed to express the operably linked gene in a prokaryotic or eukaryotic host or both (shuttle vectors) and can additionally contain transcriptional elements such as enhancer elements, termination sequences, tissue-specificity elements, and/or translational initiation and termination sites.

The terms "vectors" or "DNA construct" are commonly known in the art and refer to any genetic element, including, but not limited to, plasmid DNA, phage DNA, viral DNA and the like which can incorporate the oligonucleotide sequences, or sequences of the present invention and serve as a DNA vehicle into which DNA of the present invention can be cloned. Numerous types of vectors exist and are well known in the art.

As used herein the term "polynucleotide" of the present invention also includes those polynucleotides capable of hybridizing, under stringent hybridization conditions, to sequences herein or the complement thereof. The term "stringent hybridization conditions" is used as generally understood in the art. For example the term can mean an overnight incubation at 42° C. in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 mg/ml denatured, sheared salmon sperm DNA, followed by washing the filters in 0.1× SSC at about 60° C. The exact conditions required for "high stringency" may vary depending on the nature of the nucleic acid samples (i.e. DNA:DNA or DNA:RNA).

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M NaH2PO4; 0.02M EDTA, pH 7.4), 0.5% SDS, 30% formamide, 100 mu.g/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

As used herein, the term "host" is meant to include not only prokaryotes but also eukaryotes such as yeast, plant and animal cells. A recombinant DNA molecule or gene which encodes a protein of the present invention can be used to transform a host using any of the techniques commonly known to those of ordinary skill in the art. Prokaryotic hosts may include *E. coli,* S. tymphimurium, *Serratia marcescens* and *Bacillus subtilis.* Eukaryotic hosts include yeasts such as *Pichia pastoris,* mammalian cells and insect cells.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to arrangements of J12 splice variant which are preferably about 5 to about 15 amino acids in length. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The terms "complementary" or "complementarity," as used herein, refer to the natural binding of polynucleotides under permissive salt and temperature conditions by base pairing.

The term "homology or identity," as used herein, refers to a degree of complementarity. There may be partial homology or complete homology. A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay under conditions of reduced stringency.

The term "ortholog" refers to a polypeptide obtained from one species that corresponds to the functional counterpart of a polypeptide from another species.

The phrases "percent identity" or "% identity" refer to the percentage of sequence similarity found in a comparison of two or more amino acid or nucleic acid sequences. Percent identity can be determined electronically, e.g., by using the MEGALIGN program (Lasergene software package, DNASTAR. Inc., Madison Wis.). The MEGALIGN program can create alignments between two or more sequences according to different methods, e.g., the clustal method. (Higgins, D. G. and P. M. Sharp (1988) Gene 73:237-244). Percent identity between nucleic acid sequences can also be calculated by the clustal method, or by other methods known in the art, such as the Jotun Hein method. (See, e.g., Hein, J. (1990) Methods in Enzymology 183:626-645.) Identity between sequences can also be determined by other methods known in the art, e.g., by varying hybridization conditions.

The term "hybridization," as the term is used herein, refers to any process by which a strand of nucleic acid binds with a complementary strand through base pairing.

The conditions may be varied by adding or removing various blocking reagents. Blocking reagents can include Denhardt's reagent, heparin, BLOTTO, denatured salmon sperm DNA, and commercially available product. The inclusion of specific blocking reagents may require modification of the hybridization conditions described above, due to problems with compatibility.

The polynucleotide of the present invention can be composed of any polyribonucleotide or polydeoxyribonucleotide, which may be unmodified RNA or DNA or modified RNA or DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The term "isolated nucleic acid" as used herein refers to a nucleic acid molecule, RNA or DNA that has been removed from its environment.

The term "degenerate DNA" as used herein refers to a sequence that includes one or more degenerate codons that contain different triplets of nucleotides but encode the same amino acid residue.

The term "stringent conditions" as used herein is meant overnight incubation at 42° C. in a solution comprising: 50% formamide, 5×SSC (1.times.SSC=150 mM NaCl, 15 mM trisodium citrate), 50 mM sodium phosphate (pH 7.6), 5× Denhardt's solution, 10% dextran sulfate, and 20 mu.g/ml denatured, sheared salmon sperm DNA, followed by washing the filters in 0.1×SSC at about 65° C. or equivalent conditions.

The term "operably linked" as used herein refers to DNA segments that function together for their intended purpose.

The term "tissue" as used herein refers to one or more cells, extracts and fractions thereof.

The term "cell" as used herein refers to cells in any form, including but not limited to, cells retained in tissue, cell clusters and individually isolated cells.

The term "gene transcription" as used herein refers to a process whereby one strand of a DNA molecule is used as a template for synthesis of a complementary RNA by RNA polymerase.

The term "gene expression" as used herein refers to the process whereby information encoded in a particular gene is decoded into a particular protein. The level of gene expression as the term is used herein can be can be determined by measuring the level of mRNA in a cell.

The term "DNA" as used herein refers to polynucleotide molecules, segments or sequences and is used herein to refer to a chain of nucleotides, each containing the sugar deoxyribose and one of the four adenine (A), guanine (G) thymine (T) or cytosine (C).

The term "RNA" as used herein refers to polynucleotide molecules, segments or sequences and is used herein to refer to a chain of nucleotides each containing the sugar ribose and one of the four adenine (A), guanine (G) uracil (U) or cytosine (C).

The term "oligo" as used herein means a short sequence of DNA or DNA derivative typically 8 to 35 nucleotides in length. The exact size of the molecule will depend on many factors, which in turn depend on the ultimate function or use of the oligonucleotide. An oligonucleotide can be derived synthetically, by cloning or by amplification. The term "derivative" is intended to include any of the above described variants when comprising additional chemical moiety not normally a part of these molecules. These chemical moieties can have varying purposes including, improving a molecule's solubility, absorption, biological half life, decreasing toxicity and eliminating or decreasing undesirable side effects.

The term "autoimmune and inflammatory disease" as used herein means diseases that are associated with autoimmune and inflammatory conditions such as inflammatory and autoimmune conditions such as osteoarthritis, reperfusion injury, asthma, multiple sclerosis, Guillain-Barre syndrome, Crohn's disease, ulcerative colitis, psoriasis, graft versus host disease, systemic lupus erythematosus, rheumatoid arthritis, Alzheimer's disease, toxic shock syndrome, insulin-dependent diabetes mellitis, acute and chronic pain as well as symptoms of inflammation and cardiovascular disease, stroke, myocardial infarction alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, Grave's disease, myasthenia gravis, scleroderma and atopic dermatitis.

The term "cell line" refers to cells capable of stable growth in vitro for multiple generations.

The term "target" refers to any gene perturbed in a disease state, developmental stage or drug treatment. Frequently a target refers to a drug development target that is capable of being altered by an agent or compound. Such drug development targets are suitable for screening candidate compounds used in direct binding assays.

The term "DNA Microarray" as used herein refers collectively to a technique(s) used to measure and analyze the expression of a large number of genes simultaneously and as described in Microarray analysis Schena, Mark Wiley-Liss, 2003 incorporated herein by reference. The term can refer to DNA microarrays which contain microscopic spots of about 1 kb DNA sequences representing thousands of genes bound to the surface of glass microscopic slides. The term can also refer to oligonucleotide arrays (DNA chips) or high density nucleotide probes which contain synthetic oligonucleotides representing thousands of gene sequences synthesized on the surface of small areas of a glass slide.

EXAMPLES

Identification of J12 EST Using Microarray Analysis

The present invention relates to J12 and variants which were initially identified with microarray analysis a technique used in the art used to study the expression level of thousands of genes at the same time. Microarray analysis of Th1 and Th2 stimulated cells was used to identify differentially expressed genes between Th1 and Th2 cells. The analysis was performed with the Affymetrix Genechip system on RNA samples obtained from spleen cells derived from DO11 TCR transgenic mice. These spleen cells were stimulated with OVA and different antibodies and recombinant proteins in order to promote the differentiation of the cells into Th1 and Th2 cells. The Th1 or Th2 cells were then stimulated with anti-CD3 antibodies for 2 hours and then total RNA was prepared for microarray analysis. Preparation of the RNA samples and hybridization with the gene chip apparatus was performed according to the methods specified herein using techniques suggested by Affymetrix. The data obtained from the microarray analysis of the RNA samples was analyzed revealing that EST AK005939 (SEQ ID No. 23) exhibited Th2 specific expression. We conducted further analysis on the EST.

Identification of the Full Length J12 Mouse cDNA Sequence

Using the procedure that follows the full length cDNA corresponding to the EST was obtained. The full length mouse cDNA corresponding to the EST and IMAGE clones relating to AK005939 (SEQ ID No. 23) were obtained from the American Type culture collection and further purified and sequenced. One of Image clones corresponded to the full-length of J12.

Description of the Mouse J12 cDNA

The mouse cDNA corresponding to the EST AK005939 (SEQ ID No. 23) is shown in SEQ ID. NO. 1, however there is a 221 bp fragment inserted between $T^{237}$ and $G^{238}$ of EST AK005939 (SEQ ID No. 23). FIG. 1 shows an alignment of EST AK005939 (SEQ ID No. 23) and the mouse J12 sequence (SEQ ID No. 1). SEQ ID. No 15 is a fragment of the cDNA that does not align with EST AK005939 (SEQ ID No. 23). The mouse J12 cDNA (SEQ ID No. 1) is predicted to encode a 163 amino acid protein having a signal peptide with the cleavage site between $Gly^{30}$ and $Ala^{31}$ SEQ ID. NO. 2. See FIGS. 2A and 2B. The mouse J12 gene Genomic structure (SEQ ID No. 1) compared with AK005939 (SEQ ID No. 23) was shown in FIG. 2C.

Figure 3:
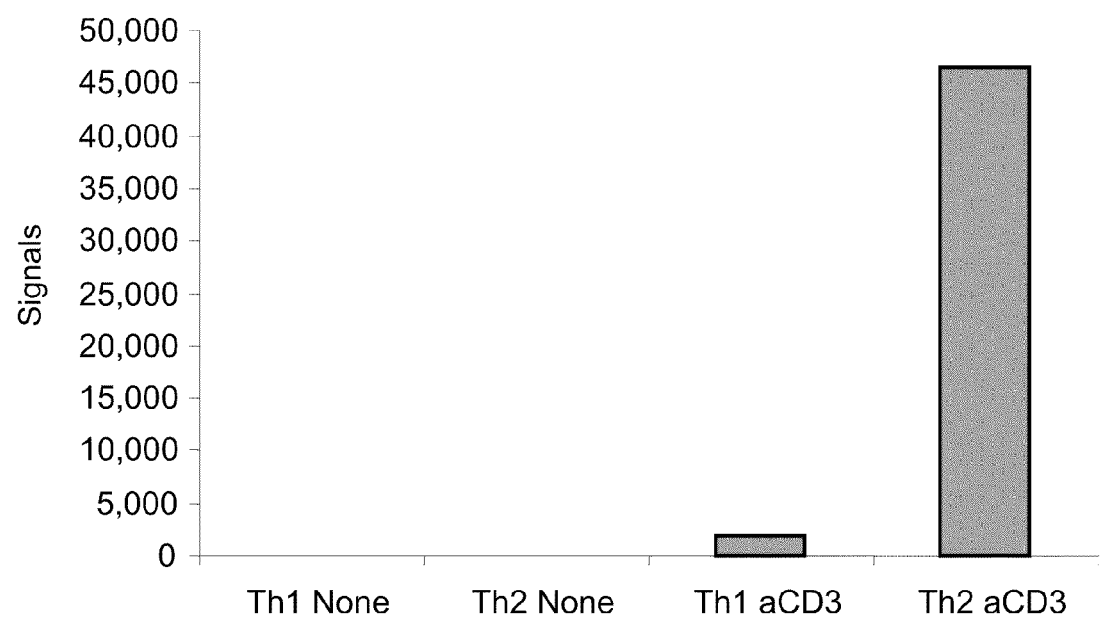
FIG. 3 shows J12 mRNA is specifically induced in mouse Th2 cells by anti-CD3 stimulation.
Figure 4:
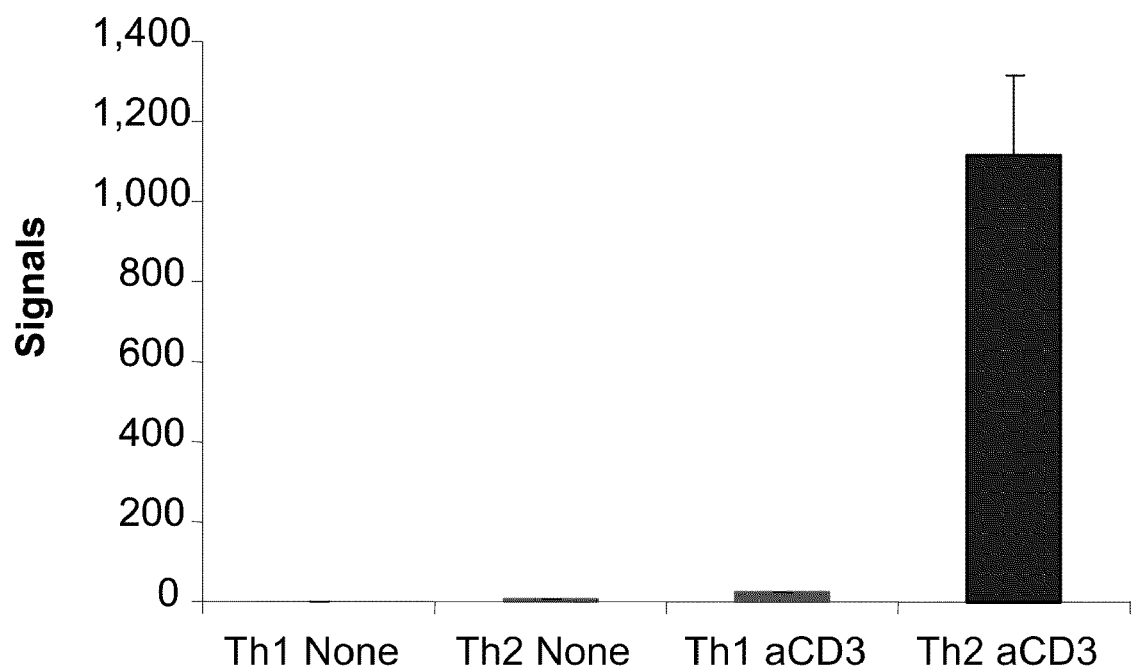
FIG. 4 shows Taqman PCR analysis of J12 mRNA expression in mouse Th2 cell stimulated by anti-CD3.

The J12 mRNA is specifically induced in mouse Th2 cells by anti-CD3 stimulation. (FIG. 3) Th1 and Th2 cells were stimulated with anti-CD3 antibodies for 2 hours before cells were harvested for total RNA extraction. Biotin-labeled cRNAs were in vitro transcribed from double strand cDNA synthesized from total RNA. The cRNAs were used to probe the Affymetrix M430 Chip A and B. After normalization, we discovered that EST AK005939 (SEQ ID No. 23), which contain part of J12 sequence (SEQ ID No. 2), is specifically expressed in Th2 cells. See FIG. 2. The results of Taqman PCR confirmed that J12 mRNA is specifically induced in mouse Th2 cell by anti-CD3 stimulation. See FIG. 4.

Figure 5:
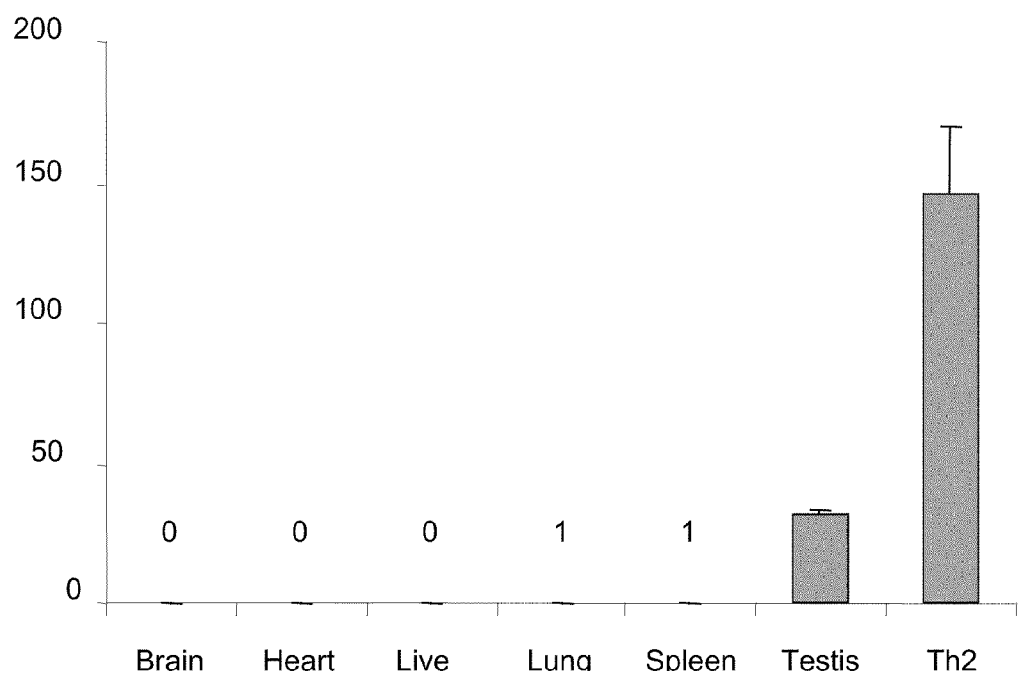
FIG. 5 shows mouse J12 mRNA expression in normal tissues.

Expression of mouse J12 cDNA in normal tissues is shown in FIG. 5. J12 is expressed predominantly in Th2 cells. J12 was also expressed at a lower level in Testes. J12 expression was at undetectable levels in the other tissues tested including brain, heart, liver, lung, and spleen.

Human J12 cDNA Variants and the Proteins they Encode for.

Having established the mouse J12 sequence (SEQ ID No. 1) it was of further interest to find the human ortholog of J12. The further interest is looking for human ortholog of mouse J12. A Blast search conducted against NCBI non-redundant database using protein sequence derived from AK005939 (SEQ ID No. 23) revealed no significant hits other than itself. The blast search conducted using mouse J12 protein sequence (SEQ ID No. 2) against the human genome showed a single hit on human chromosome 12 with statistically significant similarity. The blast hit is located on the reverse complement strand of a human gene named MGC35140. This suggests that there may be a human J12 gene missed by the current model prediction due to the overlapping with gene MGC35140 at the genomic sequence level. The GenScan prediction using a segment of genomic sequence covering the targeted region clearly indicated a new human gene encoding a longer protein sequence than the ORF derived from AK005939 (SEQ ID No. 23). It also contains a predicted signal peptide. This in turn suggested that AK005939 (SEQ ID No. 23) may not be a complete ORF or there might be other splicing variants in mouse genome which can be secreted. The GenScan prediction using a longer mouse genome fragment supported this idea and a gene model with longer ORF with signal peptide is predicted. Based on predicted human J12 we cloned the human J12 using the RACE method.

Three variants of the human J12 clone were found. These variants are designated as human J12 var1 (SEQ ID. No. 3), human J12 var2 (SEQ ID No. 4) and human J12 var3 (SEQ ID No. 5). The predicted amino acid sequence for these variants are shown in SEQ ID No's 6-8 respectively. FIG. 6a-c shows the predicted protein sequences of the human J12 variants 1-3 respectively (SEQ ID Nos. 6-8). Human J12 var1 (SEQ ID No. 3) encodes for a 275 amino acid polypeptide. Human J12 var2 (SEQ ID No. 4) encodes for a 164 amino acid polypeptide having a signal peptide cleavage site between amino acids residues 23 and 24. Human J12 var3 (SEQ ID No. 5) encodes for a 164 amino acid polypeptide. FIG. 7 shows an alignment of the coding regions and the cloned sequences for the three human J12 variants (SEQ ID Nos. 3-5). FIG. 8 shows the SMART sequence analysis of human J12 variant 1 (SEQ ID No. 6), variant 2 (SEQ ID No. 7) and variant 3 (SEQ ID No. 8) protein sequences. FIG. 9 shows an alignment of the three human J12 variants (SEQ ID Nos. 3-5) and the EST AK005939 (SEQ ID No. 23). SEQ ID No. 16 is 3 'a base fragment of J12 Var3 that does not align with EST AK005939 (SEQ ID No. 23). SEQ ID. No. 17 is a 3' base fragment of J12 Var1 that does not align with EST AK005939 (SEQ ID No. 23). SEQ ID No. 18 corresponds to 3' bases of J12 Var1. SEQ ID. No. 19 corresponds to 3' bases of human J12 Var2.

Figure 10:
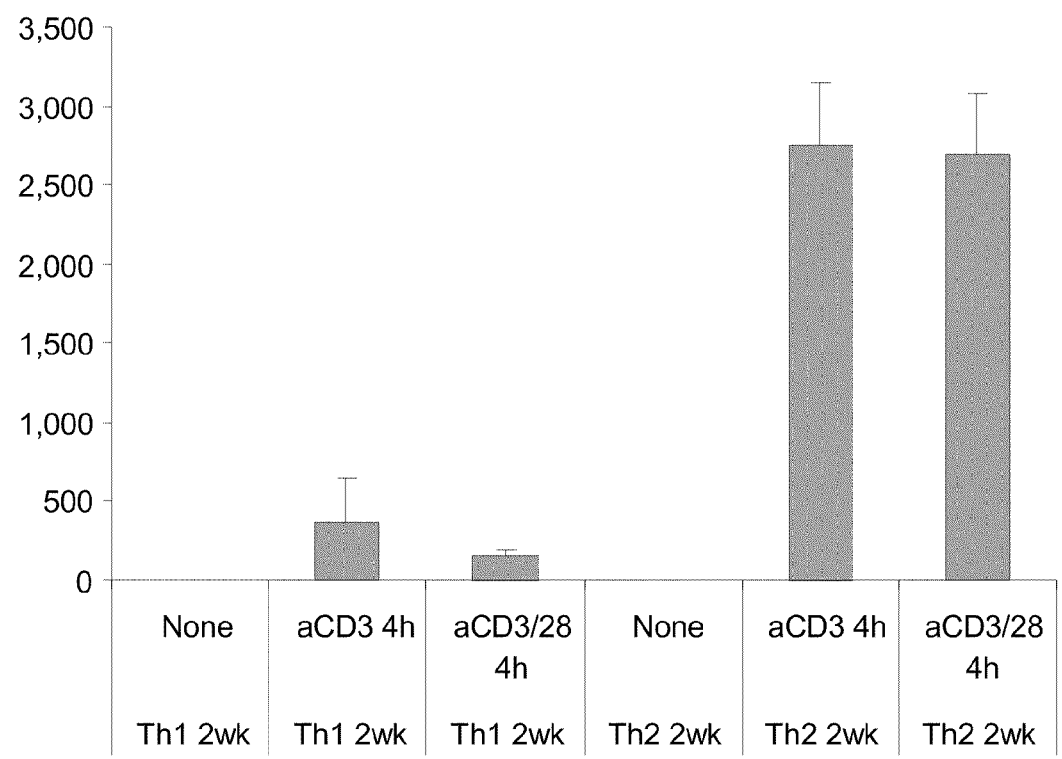
FIG. 10 shows Taqman PCR analysis of J12 mRNA expression in human Th2 cells stimulated with anti CD3/CD28 stimulation.

We confirmed that J12 is specifically expressed in human Th2 cells using Taqman PCR. See FIG. 10. Human naïve CD4+ T cells were purified from PBMC and the cells were differentiated into Th1 and Th2 cells for 2 weeks. Cells were then stimulated with anti-CD3 or anti-CD3 and anti-CD28 for 4 hours before total RNA was extracted. RT-TaqMan PCR was performed. The unstimulated (None) cells do not express J12 while J12 was highly induced in Th1 cells stimulated with anti-CD3 or anti-CD3/anti-CD28. CD28 signaling does not play an important role in J12 expression since there is no different expression of J12 between anti-CD3 and anti-CD3/anti-cD28 stimulation.

Figure 11:
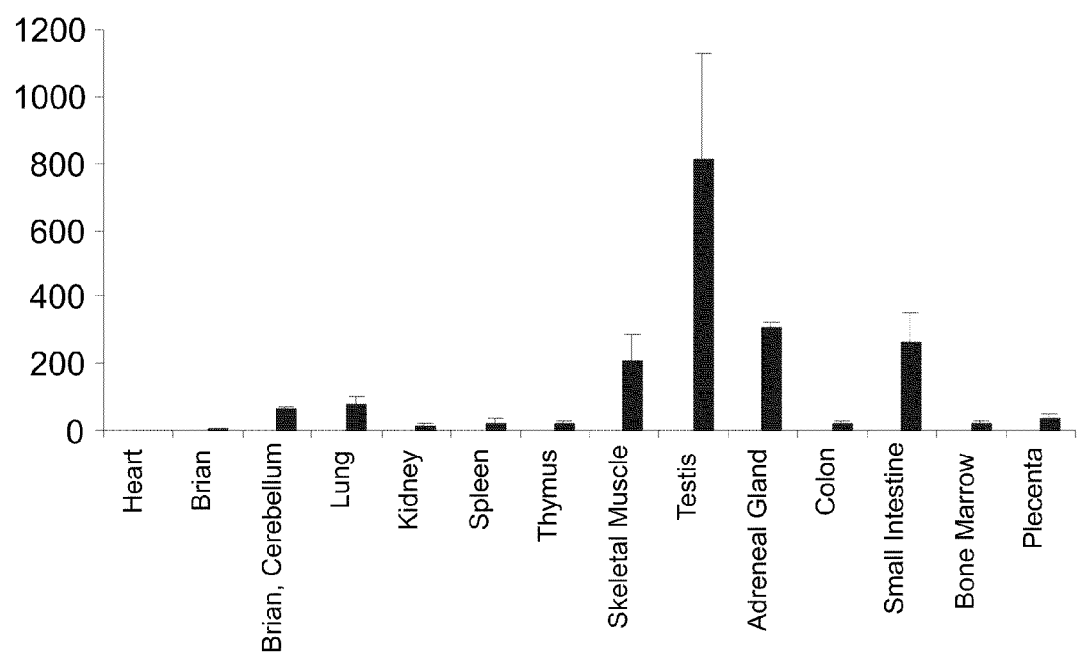
FIG. 11 shows the expression of J12 in selected normal human tissues.

J12 is expressed in selected normal human tissues is shown in FIG. 11. J12 is expressed predominantly in testes cells. It is also expressed in adrenal gland, small intestine, and skeletal muscle. J12 was expressed at lower level in brain (cerebellum), lung and placenta. J12 was expressed at very low levels in heart, brain, kidney spleen, thymus colon and bone marrow.

Homology to IL-4 and IL-13

A homology search of the human J12 sequences revealed that is a novel gene bearing homology to several human cytokines such as IL-4 and IL-13. FIG. 8 shows an alignment of human J12 variant 1, variant 2 and variant 3 partial protein sequences against the human IL-4 and IL-13 sequences.

Homology to IL-31

IL31 (Genbank accession number for the nucleic acid is AY499343) (SEQ ID No. 34) is a T cell derived cytokine disclosed in Nature Immunology, Jul. 4, 2004 and in United States Patent application No. 20030224487, published Dec. 3, 2003. FIG. 13 shows an alignment of the mouse J12 sequence (SEQ ID No. 1) to the published coding sequence for IL-31 based on from United States Patent application No. 20030224487. The sequences are identical in the coding regions except for the insertion of GGG at positions 987-999 of the Mouse J12 sequence (SEQ ID No. 1). The bases are not located in AY509149 (SEQ ID No. 33). Also, the Mouse J12 (SEQ ID No. 1) has a longer 3' and 5' UTR relative to IL-31. SEQ ID. No. 20 is mouse J12 bases 1-427. FIG. 14 shows the human J12 VAR1 (SEQ ID No. 6) aligned to the protein sequence for IL31 (AY499343) (SEQ ID No. 34). The human J12 VAR 2 has 125 additional amino acid residues at the C terminal end of the polypeptide. SEQ ID. No. 21. FIG. 15 shows human J12 var2 (Human J12-2) (SEQ ID No. 7) vs AY499343 (IL31) (SEQ ID No. 34) amino acid sequences and that the sequences are identical. FIG. 16 shows human J12 var3 (Human J12-3) (SEQ ID No. 8) vs AY499343 (IL31) (SEQ ID No. 34) amino acid sequences. Human J12 var1 has 111 more amino acids than human AY499343 (IL31) (SEQ ID No. 34). SEQ ID. No. 22.

The first 350 bases of SEQ ID. No. 3 do not match the IL-31 sequence (SEQ ID No. 34). The first 597 bases of SEQ ID No. 5 do not match the IL-31 sequence (SEQ ID No. 34).

Functions of J12

J12 is differentially expressed in activated Th2 cells and therefore serves as a marker for Th2 stimulated cells that are associated with diseases such as Asthma. There are several possible functions for the J12 protein including the possible involvement in Th1 and Th2 cytokine production, such as interferon γ, IL2, TNFα, IL4, IL5, IL10 and IL13, and in T cell homeostasis (proliferation and apoptosis). As a secreted or cell-surface protein J12 could also function as pro-inflammatory mediators (adhesion, chemotaxis, growth factor) for other cell types.

Methods of Making Antibodies to J12

Polycolonal or monoclonal antibodies against J12 could be used to perform Western blot, immunoprecipitation, immunohistochemistry and FACS analysis. Methods for making polyclonal and monoclonal antibodies against polypeptides are known in the art and are described in Current Protocols in Immunology, 2004 by John Wiley & Sons, Inc. the contents of which is incorporated herein. Importantly, they could be used to neutralize J12 activity in vitro and in vivo if they are neutralizing antibodies. The neutralizing antibodies could be used to treat several diseases such as autoimmune and inflammatory diseases.

Human and mouse J12 short peptides and whole protein will be used to immunize animals to produce antibodies. Short peptides will be chemically synthesized and conjugated to KLH. The conjugated J12-KLH will be mixed in CFA (Complete Freund's adjuvant). The J12-KLH-CFA mix will be intradermally injected into rabbits for polyclonal antibody production. The rabbits will be boosted with J12-KLH mixed with IFA (Incomplete Freud's adjuvant) every 4 weeks. The antibody titer in the blood will be detected by ELISA. Once high titers of J12 antibody detected, the animals will be sacrificed and the J12 antibodies in the blood will be purified by affinity purification. Whole J12 recombinant proteins will also used to immunize the animals. J12 protein will mixed with CFA as described and the same procedure will be performed as above. For the generation of monoclonal antibodies, rats or mice will be immunized with J12 peptide-KLH or J12 protein. Recombinant humanized J12 monoclonal antibodies will be finally used to treat human diseases.

Methods of RNA Isolation

Methods of RNA isolation are well known in the art and the RNA isolation method used should depend on the source of the cells. See Maniatis et al, Molecular *Cloning: A Laboratory Manual*, Third Edition (2001) (Cold Spring Harbor Press, Cold Spring Harbor, N.Y.). The preferred method of RNA isolation is the Qiagen RNA purification kit. (Qiagen, Valencia, Calif.).

Steps should be taken to avoid degradation of the RNA prior to analysis. Typically, RNA is isolated from cells soon after the cells have been collected for analysis. Cells that have been collected should be stored under conditions that limit the degradation of RNA known to those skilled in the art. Likewise, after RNA has been isolated from the cell samples the RNA should be stored under conditions that reduce RNA degradation. For example, RNA should be stored on dry ice or under $-70°$ C. conditions under RNAse free conditions. DEPC water should be used in buffers and solutions. Conditions should also be maintained such that additional RNA synthesis is terminated when the cells are collected. In this way RNA expression will be representative of the types and levels of RNA expression at the time of collection.

Isolated RNA from the cells is used to synthesize double stranded DNA in a reverse transcriptase reaction that can be performed according to methods known to those skilled in the art. The preferred reverse transcriptase is the Superscript reverse transcriptase (Superscript Choice™, Invitrogen Carlsbad, Calif.). It is used according the manufacturers instructions. Approximately 5 to 15 μg total RNA from each time points are used to measure in reverse transcriptase reactions. The amount of RNA used varies depending on the number of genes tested and the method used to detect gene expression.

The cDNA is used as a template for the synthesis of labeled cRNA with a plasmid or vector. The cRNA can be labeled with fluorescence or with other methods commonly used in the art such as for labeling nucleic acids. The cRNA is most preferably labeled with biotin. The cRNA is then fragmented using an alkaline base method commonly used in the art.

Preferred Embodiment of the Invention

The following examples are provided to illustrate the invention, but not to limit its scope. Other variants of the invention will be readily apparent to one of ordinary skill in the art. The contents of all references, patents and published patent applications cited throughout this application, as well as the figures and sequence listing are hereby incorporated by reference.

Preparation of the Cells and RNA Samples

DO11.10 transgenic spleen cells were cultured in Iscove's DME medium plus 10% FCS, L-Glutamine (2 mM), NEAA (0.1 mM), Na Pyruvate (1 mM) and 2-mercaptoethonol (0.05 mM) in the presence of recombinant IL2 (2 ng/ml, eBioscience) at a concentration of $5 \times 10^5$/ml. Cells were stimulated with the TCR specific antigen OVA (Ovalbumin, 500 μg/ml). For Th1 differentiation, the culture were added with recombinant IL-12 (5 ng/ml, CALBIOCHEM) and anti-IL4 (11B11) (2 μg/ml, eBioscience). For Th2 differentiation, recombinant IL-4 (10 ng/ml, CALBIOCHEM) and anti-IL-12 (1 μg/ml, Cell Sciences) were added into the culture. At day 7 cells were differentiated into Th1 and Th2 cells. The cells were then harvested, washed, counted and resuspended in the culture medium without IL2 at a concentration of $2 \times 10^6$/ml. Cells were stimulated with plate bound anti-CD3 antibody (10 μg/ml) for 4 hours before harvesting for total RNA extraction. Some cells were restimulated with OVA and irradiated BALB/c splenic cells (2000 rad) for another 7 day. Cells were then harvested and restimulated with anti-CD3 for 4 hours before harvesting for total RNA extraction.

RNA was isolated using the RNeasy total RNA isolation kit from Qiagen and a reverse transcription reaction was run on 1 μg of RNA using the RT kit supplied by Applied Biosystems (Foster City, Calif.) in the following manner. Each reaction contained 1×RT buffer, 5.5 mM MgCl2, 500 μM of each dNTP, 2.5 μM of Random Hexamers, 0.4 U/μl of RNase inhibitor, and 1.25 U/μl of MultiScribe Reverse Transcriptase. RT reactions were carried out at 25° C. for 10 min, 48° C. for 40 min and 95° C. for 5 min.

Microarray Analysis of RNA Samples

TaqMan real-time PCR was performed in a MicroAmp Optical 96-Well Reaction Plate (Applied Biosystems). Each well contained 4 μl of each RT product, 1× TaqMan master mix (Applied Biosystem or Eurogentec), primers (forward and reverse), and TaqMan FAM MGB probe in a total volume of 25 μl. Amplification conditions were 2 min at 50° C. (for AmpErase UNG incubation to remove any uracil incorporated into the cDNA), 10 min at 95° C. (for AmpliTaq™ Gold activation), and then run for 40 cycles at 95° C. for 15 seconds, 60° C. for 1 min. All reactions were performed in the ABI Prism 7700 Sequence Detection System for the test samples, standards, and no template controls. They were run in duplicates using the Sequence Detector V 1.6 program. The Rn and Ct were averaged from the values obtained in each reaction. A standard curve was constructed by plotting the Ct vs. the known copy numbers of the template in the standard. According to the standard curve, the copy numbers for all unknown samples were obtained automatically. To determine the copy numbers of the target transcript, a mouse or human genomic DNA (Clontech, Palo Alto, Calif.) was used to generate a standard curve. The copy numbers of genomic DNA template were calculated according to the molecular weight of human diploid genome [$3\times10^9$ bp=$3\times10^9\times660$ (M.W.)=$2\times10^{12}$ g], and then 1 µg/µl genomic DNA was converted into $2.4\times10^6$ copy numbers based upon the Avogadro's number (1 mol=$6.022\times10^{23}$ molecules). The genomic DNA was diluted every ten-fold at a range of $5\times10^5$ to $5\times10^0$ copy numbers. Each sample was run in duplicates, and the Rn (the ratio of the amount of reporter dye emission to the quenching dye emission) and threshold cycle (Ct) values were averaged from each reaction. The copy numbers were then normalized to GAPDH to minimize variability in the results due to differences in the RT efficiency and RNA integrity among tests.

Th1 cells expressed a high level of IFN-γ and low levels of IL-4 when cells were stimulated with anti-CD3, while Th2 cells expressed higher level of IL-4 and low IFN-γ after stimulation with anti-CD3.

Finally, the The cRNA was prepared according to standard protocols provided by the Affymetrix. The cRNA was hybridized onto the murine and murine M430 chip B.

The TaqMan mix of IFNγ and IL-4 was purchased from Applied Biosystems. The J12 TaqMan primers and probe are described as follows:

```
1) Mouse J12 TaqMan primers
                                        SEQ ID No. 9
   AK005939-F: GGATGTCAGCAGACGAATCAATAC
                                        SEQ ID No. 10
   AK005939-R: TTGACTTTCTCCAGATGTGCTATGA 2) Mouse J12 TaqMan ® FAM-MGB probe:
                                        SEQ ID No. 11
   AK005939-447T CAGCCTGGACCGGGAAGCATTAACC 3) Human J12 TaqMan primers:
                                        SEQ ID No. 12
   H-J12-19F: GTGCTCGTGTCCCAGAATTACAC;
                                        SEQ ID No. 13
   H-J12-R:   TGTCTAGCTGTCTGATTGTCTTGAGATA 4) Human J12 TaqMan® FAM-MGB probe:
                                        SEQ ID No 14
   H-J12-Probe: TCCACAGCCCAGCCATCCGG.
```

---

The invention claimed is:

1. An isolated nucleic acid comprising a sequence that encodes a polypeptide with the amino acid sequence of SEQ ID No. 8.

2. An expression vector comprising the nucleic acid of claim 1 operably linked to an expression control sequence.

3. A cultured cell comprising the vector of claim 2.

4. A method of producing a protein comprising culturing a cell of claim 3 under conditions permitting expression of the polypeptide.

* * * * *

SEQUENCE LISTING

<160> NUMBER OF SEQ ID NOS: 34

<210> SEQ ID NO 1
<211> LENGTH: 1249
<212> TYPE: DNA
<213> ORGANISM: Mus musculus

<400> SEQUENCE: 1

```
agaacgcaag gacaagggca ggccctggag cacagatgcc ttctccttat gccttccctg      60
tgttcactag agccatcccc ctgcctccgg aattcccaca gatggatcgc tctgtggctt     120
cttaaaactt ccctgcaggg cactgaccct cagcccctct aagtcacttc ttccccagtg     180
attgtacttt tcaatcgggc ttcaaacttt cctctcatta aatcagcaag cactttccaa     240
gaaaagagag atgctcaaga tgccttcctg tgtgccctgc tttccccagg ccgagccgag     300
gctggcaacc ttttgaaaat gttttctgga gaaaagctga gcaatggttt tgccatgggc     360
gggcctttga tctgcttcct catgacaacc ctttatatat tgcctggtgg ccatggcgaa     420
cacaccaggc tccagagacc acaggcaaag cgggccttcc tcactctctt accgtcgcca     480
tgatcttcca cacaggaaca acgaagccta ccctggtgct gctttgctgt ataggaacct     540
ggctggccac ctgcagcttg tccttcggtg ccccaatatc gaaggaagac ttaagaacta     600
caattgacct cttgaaacaa gagtctcagg atctttataa caactatagc ataaagcagg     660
catctgggat gtcagcagac gaatcaatac agctgccgtg tttcagcctg gaccgggaag     720
cattaaccaa catctcggtc atcatagcac atctggagaa agtcaaagtg ttgagcgaga     780
acacagtaga tacttcttgg gtgataagat ggctaacaaa catcagctgt ttcaacccac     840
tgaatttaaa catttctgtg cctggaaata ctgatgaatc ctatgattgt aaagtgttcg     900
tgcttacggt tttaaagcag ttctcaaact gcatggcaga actgcaggct aaggacaata     960
ctacatgctg agtgatgggg ggggggggt gcagtgtcct cagcagtgcc tgtccttcga    1020
gggctgagct tgcaacccag gacttaactc caaagggact gtgcggtcat tactagtcat    1080
gttatttatg ttttttatttt gtccactgaa atcttgttct gctaccctgt agggactgga    1140
agtggcagct atatttattt atttatgtac tgagtttgtt aacgctccat ggaggagcct    1200
tcagagtcta tttaataaat tatattgaca tgaaaaaaaa aaaaaaaa               1249
```

<210> SEQ ID NO 2
<211> LENGTH: 163
<212> TYPE: PRT
<213> ORGANISM: Homo sapiens

<400> SEQUENCE: 2

```
Met Ile Phe His Thr Gly Thr Thr Lys Pro Thr Leu Val Leu Leu Cys
1               5                   10                  15

Cys Ile Gly Thr Trp Leu Ala Thr Cys Ser Leu Ser Phe Gly Ala Pro
            20                  25                  30

Ile Ser Lys Glu Asp Leu Arg Thr Thr Ile Asp Leu Leu Lys Gln Glu
        35                  40                  45

Ser Gln Asp Leu Tyr Asn Asn Tyr Ser Ile Lys Gln Ala Ser Gly Met
    50                  55                  60

Ser Ala Asp Glu Ser Ile Gln Leu Pro Cys Phe Ser Leu Asp Arg Glu
65                  70                  75                  80

Ala Leu Thr Asn Ile Ser Val Ile Ile Ala His Leu Glu Lys Val Lys
                85                  90                  95

Val Leu Ser Glu Asn Thr Val Asp Thr Ser Trp Val Ile Arg Trp Leu
            100                 105                 110

Thr Asn Ile Ser Cys Phe Asn Pro Leu Asn Leu Asn Ile Ser Val Pro
        115                 120                 125

Gly Asn Thr Asp Glu Ser Tyr Asp Cys Lys Val Phe Val Leu Thr Val
    130                 135                 140

Leu Lys Gln Phe Ser Asn Cys Met Ala Glu Leu Gln Ala Lys Asp Asn
145                 150                 155                 160

Thr Thr Cys
```

<210> SEQ ID NO 3
<211> LENGTH: 878
<212> TYPE: DNA
<213> ORGANISM: Homo sapiens

<400> SEQUENCE: 3

```
ggggcagggg cctctccagg cgctctcacc tgccccgagg gaaaagtccc ccatccggat    60
cagacagcct ggccccaacc acctgcgttt tctcttctgc cctcatctat aaaaatggga   120
taacagctgg tggttctaag tgcggcagct cccgcaggca ttccttccta cacgcttcag   180
atccacacgt ccgacagcct actgtgtgtc ttcagctgag catccataac acttcccatt   240
cactgtgtca aaagctgaat caggccgggc acgtggcttg cacctacagt cgcagcactt   300
tgggaggcca aggcagccat ggcgaacaca tctggctcca gaagccccca ctgaagctgg   360
ccttgctctc tctcgccatg gcctctcact caggcccctc gacgtctgtg ctctttctgt   420
tctgctgcct gggaggctgg ctggcctccc acacgttgcc cgtccgttta ctacgaccaa   480
gtgatgatgt acagaaaata gtcgaggaat acagtccct ctcgaagatg cttttgaaag   540
atgtggagga agagaagggc gtgctcgtgt cccagaatta cacgctgccg tgtctcagcc   600
ctgacgccca gccgccaaac aacatccaca gcccagccat ccgggcatat ctcaagacaa   660
tcagacagct agacaacaaa tctgttattg atgagatcat agagcacctc gacaaactca   720
tatttcaaga tgcaccagaa acaaacattt ctgtgccaac agcacccat gaatgtaaac   780 gcttcatcct gactatttct caacagtttt cagagtgcat ggacctcgca ctaaaatcat   840
tgacctctgg agcccaacag gccaccactt aaaataaa                            878
```

```
<210> SEQ ID NO 4
<211> LENGTH: 721
<212> TYPE: DNA
<213> ORGANISM: Homo sapiens

<400> SEQUENCE: 4
ggcgctctca cctgccccga gggaaaagtc ccccatccgg atcagacagc ctggccccaa      60
ccacctgcgt tttctcttct gccctcatct ataaaaatgg ataacagct ggtggttcta     120 agtgcggcag ctcccgcagg caccagcaac agcaggcagc catggcgaac acatctggct     180
ccagaagccc ccactgaagc tggccttgct ctctctcgcc atggcctctc actcaggccc     240
ctcgacgtct gtgctctttc tgttctgctg cctggggaggc tggctggcct cccacacgtt     300
gcccgtccgt ttactacgac caagtgatga tgtacagaaa atagtcgagg aattacagtc     360
cctctcgaag atgcttttga agatgtgga ggaagagaag ggcgtgctcg tgtcccagaa     420
ttacacgctg ccgtgtctca gccctgacgc cagccgcca acaacatcc acagcccagc     480 catccgggca tatctcaaga caatcagaca gctagacaac aaatctgtta ttgatgagat     540
catagagcac ctcgacaaac tcatatttca agatgcacca gaaacaaaca tttctgtgcc     600
aacagacacc catgaatgta acgcttcat cctgactatt tctcaacagt tttcagagtg     660
catggacctc gcactaaaat cattgacctc tggagcccaa caggccacca cttaaaataa     720
a                                                                    721

<210> SEQ ID NO 5
<211> LENGTH: 1120
<212> TYPE: DNA
<213> ORGANISM: Homo sapiens

<400> SEQUENCE: 5
ccccatccgg atcagacagc ctggccccaa ccacctgcgt tttctcttct gccctcatct      60
ataaaaatgg ataacagct ggtggttcta agtgcggcag ctcccgcagg caacagggtt     120
tcaccatgtt ggccaggatg gtctcgacct tttgacctcg tgatccgccc gcctcggcct     180
cccaaagtgc tgggattaca ggcgtgagcc accgcaccca gccttctttt tctcttgaga     240
gtgccttctc catgttctag attaaatcat catcttctcc ttgtcctgtt aatggaagca     300
tgtcccaggg ctccacacga cttccacacc tcacactgct catctcttac tggcttacag     360
ttttatctgc cacaatacct tgatggcacc cacatttaca tctgtagttc cttcctacac     420
gcttcagatc cacacgtccg acagcctact gtgtgtcttc agctgagcat ccataacact     480
tcccattcac tgtgtcaaaa gctgaatcag gccgggcacg tggcttgcac ctacagtcgc     540
agcactttgg gaggccaagg cagccatggc gaacacatct ggctccagaa gcccccactg     600
aagctggcct tgctctctct cgccatggcc tctcactcag gccctcgac gtctgtgctc     660 tttctgttct gctgcctggg aggctggctg gcctcccaca cgttgcccgt ccgtttacta     720
cgaccaagtg atgatgtaca gaaaatagtc gaggaattac agtccctctc gaagatgctt     780
ttgaaagatg tggaggaaga aagggcgtg tccgtgtccc agaattacac gctgccgtgt     840
ctcagccctg acgccagcc gccaaacaac atccacagcc cagccatccg gcatatctc     900 aagacaatca gacagctaga caacaaatct gttattgatg agatcataga gcacctcgac     960
aaactcatat ttcaagatgc accagaaaca aacatttctg tgccaacaga cacccatgaa    1020
tgtaaacgct tcatcctgac tatttctcaa cagttttcag agtgcatgga cctcgcacta    1080
aaatcattga cctctggagc ccaacaggcc accacttaaa                          1120
```

```
<210> SEQ ID NO 6
<211> LENGTH: 289
<212> TYPE: PRT
<213> ORGANISM: Homo sapiens

<400> SEQUENCE: 6

Gly Arg Gly Leu Ser Arg Ser His Leu Pro Arg Gly Lys Ser Pro
1               5                   10                  15

Pro Ser Gly Ser Asp Ser Leu Ala Pro Thr Thr Cys Val Phe Ser Ser
            20                  25                  30

Ala Leu Ile Tyr Lys Asn Gly Ile Thr Ala Gly Gly Ser Lys Cys Gly
                35                  40                  45

Ser Ser Arg Arg His Ser Phe Leu His Ala Ser Asp Pro His Val Arg
    50                  55                  60

Gln Pro Thr Val Cys Leu Gln Leu Ser Ile His Asn Thr Ser His Ser
65                  70                  75                  80

Leu Cys Gln Lys Leu Asn Gln Ala Gly His Val Ala Cys Thr Tyr Ser
                85                  90                  95

Arg Ser Thr Leu Gly Gly Gln Gly Ser His Gly Glu His Ile Trp Leu
            100                 105                 110

Gln Lys Pro Pro Leu Lys Leu Ala Leu Leu Ser Leu Ala Met Ala Ser
        115                 120                 125

His Ser Gly Pro Ser Thr Ser Val Leu Phe Leu Phe Cys Cys Leu Gly
    130                 135                 140

Gly Trp Leu Ala Ser His Thr Leu Pro Val Arg Leu Leu Arg Pro Ser
145                 150                 155                 160

Asp Asp Val Gln Lys Ile Val Glu Glu Leu Gln Ser Leu Ser Lys Met
                165                 170                 175

Leu Leu Lys Asp Val Glu Glu Lys Gly Val Leu Val Ser Gln Asn
            180                 185                 190

Tyr Thr Leu Pro Cys Leu Ser Pro Asp Ala Gln Pro Pro Asn Asn Ile
        195                 200                 205

His Ser Pro Ala Ile Arg Ala Tyr Leu Lys Thr Ile Arg Gln Leu Asp
    210                 215                 220

Asn Lys Ser Val Ile Asp Glu Ile Glu His Leu Asp Lys Leu Ile
225                 230                 235                 240

Phe Gln Asp Ala Pro Glu Thr Asn Ile Ser Val Pro Thr Asp Thr His
                245                 250                 255

Glu Cys Lys Arg Phe Ile Leu Thr Ile Ser Gln Gln Phe Ser Glu Cys
            260                 265                 270

Met Asp Leu Ala Leu Lys Ser Leu Thr Ser Gly Ala Gln Gln Ala Thr
        275                 280                 285

Thr

<210> SEQ ID NO 7
<211> LENGTH: 164
<212> TYPE: PRT
<213> ORGANISM: Homo sapiens

<400> SEQUENCE: 7

Met Ala Ser His Ser Gly Pro Ser Thr Ser Val Leu Phe Leu Phe Cys
1               5                   10                  15

Cys Leu Gly Gly Trp Leu Ala Ser His Thr Leu Pro Val Arg Leu Leu
            20                  25                  30

Arg Pro Ser Asp Asp Val Gln Lys Ile Val Glu Glu Leu Gln Ser Leu
        35                  40                  45
```

```
Ser Lys Met Leu Leu Lys Asp Val Glu Glu Lys Gly Val Leu Val
 50                  55                  60

Ser Gln Asn Tyr Thr Leu Pro Cys Leu Ser Pro Asp Ala Gln Pro Pro
 65                  70                  75                  80

Asn Asn Ile His Ser Pro Ala Ile Arg Ala Tyr Leu Lys Thr Ile Arg
                 85                  90                  95

Gln Leu Asp Asn Lys Ser Val Ile Asp Glu Ile Ile Glu His Leu Asp
                100                 105                 110

Lys Leu Ile Phe Gln Asp Ala Pro Glu Thr Asn Ile Ser Val Pro Thr
            115                 120                 125

Asp Thr His Glu Cys Lys Arg Phe Ile Leu Thr Ile Ser Gln Gln Phe
            130                 135                 140

Ser Glu Cys Met Asp Leu Ala Leu Lys Ser Leu Thr Ser Gly Ala Gln
145                 150                 155                 160

Gln Ala Thr Thr

<210> SEQ ID NO 8
<211> LENGTH: 275
<212> TYPE: PRT
<213> ORGANISM: Homo sapiens

<400> SEQUENCE: 8

Met Glu Ala Cys Pro Arg Ala Pro His Asp Phe His Thr Ser His Cys
 1               5                  10                  15

Ser Ser Leu Thr Gly Leu Gln Phe Tyr Leu Pro Gln Tyr Leu Asp Gly
                 20                  25                  30

Thr His Ile Tyr Ile Cys Ser Ser Phe Leu His Ala Ser Asp Pro His
             35                  40                  45

Val Arg Gln Pro Thr Val Cys Leu Gln Leu Ser Ile His Asn Thr Ser
 50                  55                  60

His Ser Leu Cys Gln Lys Leu Asn Gln Ala Gly His Val Ala Cys Thr
 65                  70                  75                  80

Tyr Ser Arg Ser Thr Leu Gly Gly Gln Gly Ser His Gly Glu His Ile
                 85                  90                  95

Trp Leu Gln Lys Pro Pro Leu Lys Leu Ala Leu Leu Ser Leu Ala Met
                100                 105                 110

Ala Ser His Ser Gly Pro Ser Thr Ser Val Leu Phe Leu Phe Cys Cys
            115                 120                 125

Leu Gly Gly Trp Leu Ala Ser His Thr Leu Pro Val Arg Leu Leu Arg
            130                 135                 140

Pro Ser Asp Asp Val Gln Lys Ile Val Glu Glu Leu Gln Ser Leu Ser
145                 150                 155                 160

Lys Met Leu Leu Lys Asp Val Glu Glu Lys Gly Val Leu Val Ser
                165                 170                 175

Gln Asn Tyr Thr Leu Pro Cys Leu Ser Pro Asp Ala Gln Pro Pro Asn
            180                 185                 190

Asn Ile His Ser Pro Ala Ile Arg Ala Tyr Leu Lys Thr Ile Arg Gln
        195                 200                 205

Leu Asp Asn Lys Ser Val Ile Asp Glu Ile Ile Glu His Leu Asp Lys
    210                 215                 220

Leu Ile Phe Gln Asp Ala Pro Glu Thr Asn Ile Ser Val Pro Thr Asp
225                 230                 235                 240

Thr His Glu Cys Lys Arg Phe Ile Leu Thr Ile Ser Gln Gln Phe Ser
                245                 250                 255

Glu Cys Met Asp Leu Ala Leu Lys Ser Leu Thr Ser Gly Ala Gln Gln
```

Ala Thr Thr
    275

<210> SEQ ID NO 9
<211> LENGTH: 24
<212> TYPE: DNA
<213> ORGANISM: Homo sapiens

<400> SEQUENCE: 9
ggatgtcagc agacgaatca atac                                          24

<210> SEQ ID NO 10
<211> LENGTH: 25
<212> TYPE: DNA
<213> ORGANISM: Homo sapiens

<400> SEQUENCE: 10
ttgactttct ccagatgtgc tatga                                         25

<210> SEQ ID NO 11
<211> LENGTH: 25
<212> TYPE: DNA
<213> ORGANISM: Homo sapiens

<400> SEQUENCE: 11
cagcctggac cgggaagcat taacc                                         25

<210> SEQ ID NO 12
<211> LENGTH: 23
<212> TYPE: DNA
<213> ORGANISM: Homo sapiens

<400> SEQUENCE: 12
gtgctcgtgt cccagaatta cac                                           23

<210> SEQ ID NO 13
<211> LENGTH: 28
<212> TYPE: DNA
<213> ORGANISM: Homo sapiens

<400> SEQUENCE: 13
tgtctagctg tctgattgtc ttgagata                                      28

<210> SEQ ID NO 14
<211> LENGTH: 20
<212> TYPE: DNA
<213> ORGANISM: Homo sapiens

<400> SEQUENCE: 14
tccacagccc agccatccgg                                               20

<210> SEQ ID NO 15
<211> LENGTH: 221
<212> TYPE: DNA
<213> ORGANISM: Homo sapiens

<400> SEQUENCE: 15
ccctgctttc cccaggccga gccgaggctg gcaacctttt gaaaatgttt tctggagaaa    60
agctgagcaa tggttttgcc atgggcgggc ctttgatctg cttcctcatg acaaccccttt  120 atatattgcc tggtggccat ggcgaacaca ccaggctcca gagaccacag gcaaagcggg    180
ccttcctcac tctcttaccg tcgccatgat cttccacaca g                        221

<210> SEQ ID NO 16
<211> LENGTH: 251
<212> TYPE: DNA
<213> ORGANISM: Homo sapiens

<400> SEQUENCE: 16

```
cccatccgga tcagacagcc tggccccaac cacctgcgtt ttctcttctg ccctcatcta      60
taaaaatggg ataacagctg gtggttctaa gtgcggcagc tcccgcaggc aacagggttt     120
caccatgttg gccaggatgg tctcgacctt ttgacctcgt gatccgcccg cctcggcctc     180
ccaaagtgct gggattacag gcgtgagcca ccgcacccag ccttcttttt ctcttgagag     240
tgccttctcc a                                                          251
```

<210> SEQ ID NO 17
<211> LENGTH: 350
<212> TYPE: DNA
<213> ORGANISM: Homo sapiens

<400> SEQUENCE: 17

```
ccccatccgg atcagacagc ctggccccaa ccacctgcgt tttctcttct gccctcatct      60
ataaaatgg gataacagct ggtggttcta agtgcggcag ctcccgcagg caacagggtt      120
tcaccatgtt ggccaggatg gtctcgacct tttgacctcg tgatccgccc gcctcggcct    180
cccaaagtgc tgggattaca ggcgtgagcc accgcaccca gccttctttt tctcttgaga    240
gtgccttctc catgttctag attaaatcat catcttctcc ttgtcctgtt aatggaagca    300
tgtcccaggg ctccacacga cttccacacc tcacactgct catctcttac                 350
```

<210> SEQ ID NO 18
<211> LENGTH: 98
<212> TYPE: DNA
<213> ORGANISM: Homo sapiens

<400> SEQUENCE: 18

```
ggggcagggg cctctccagg cgctctcacc tgccccgagg gaaaagtccc ccatccggat      60
cagacagcct ggccccaacc acctgcgttt tctcttct                              98
```

<210> SEQ ID NO 19
<211> LENGTH: 80
<212> TYPE: DNA
<213> ORGANISM: Homo sapiens

<400> SEQUENCE: 19

```
ggcgctctca cctgccccga gggaaaagtc cccatccgg atcagacagc ctggccccaa       60
ccacctgcgt tttctcttct                                                  80
```

<210> SEQ ID NO 20
<211> LENGTH: 427
<212> TYPE: DNA
<213> ORGANISM: Homo sapiens

<400> SEQUENCE: 20

```
agaacgcaag gacaagggca ggccctggag cacagatgcc ttctccttat gccttccctg      60
tgttcactag agccatcccc ctgcctccgg aattcccaca gatggatcgc tctgtggctt     120
cttaaaactt ccctgcaggg cactgaccct cagcccctct aagtcacttc ttccccagtg    180
attgtacttt tcaatcgggc ttcaaacttt cctctcatta aatcagcaag cactttccaa    240
gaaaagagag atgctcaaga tgccttcctg tgtgccctgc tttccccagg ccgagccgag    300
```

```
gctggcaacc ttttgaaaat gttttctgga gaaaagctga gcaatggttt tgccatgggc    360
gggcctttga tctgcttcct catgacaacc ctttatatat tgcctggtgg ccatggcgaa    420
cacacca                                                              427
```

<210> SEQ ID NO 21
<211> LENGTH: 125
<212> TYPE: PRT
<213> ORGANISM: Homo sapiens

<400> SEQUENCE: 21

```
Gly Arg Gly Leu Ser Arg Arg Ser His Leu Pro Arg Gly Lys Ser Pro
1               5                   10                  15

Pro Ser Gly Ser Asp Ser Leu Ala Pro Thr Thr Cys Val Phe Ser Ser
            20                  25                  30

Ala Leu Ile Tyr Lys Asn Gly Ile Thr Ala Gly Gly Ser Lys Cys Gly
        35                  40                  45

Ser Ser Arg Arg His Ser Phe Leu His Ala Ser Asp Pro His Val Arg
    50                  55                  60

Gln Pro Thr Val Cys Leu Gln Leu Ser Ile His Asn Thr Ser His Ser
65                  70                  75                  80

Leu Cys Gln Lys Leu Asn Gln Ala Gly His Val Ala Cys Thr Tyr Ser
                85                  90                  95

Arg Ser Thr Leu Gly Gly Gln Gly Ser His Gly Glu His Ile Trp Leu
            100                 105                 110

Gln Lys Pro Pro Leu Lys Leu Ala Leu Leu Ser Leu Ala
        115                 120                 125
```

<210> SEQ ID NO 22
<211> LENGTH: 111
<212> TYPE: PRT
<213> ORGANISM: Homo sapiens

<400> SEQUENCE: 22

```
Met Glu Ala Cys Pro Arg Ala Pro His Asp Phe His Thr Ser His Cys
1               5                   10                  15

Ser Ser Leu Thr Gly Leu Gln Phe Tyr Leu Pro Gln Tyr Leu Asp Gly
            20                  25                  30

Thr His Ile Tyr Ile Cys Ser Ser Phe Leu His Ala Ser Asp Pro His
        35                  40                  45

Val Arg Gln Pro Thr Val Cys Leu Gln Leu Ser Ile His Asn Thr Ser
    50                  55                  60

His Ser Leu Cys Gln Lys Leu Asn Gln Ala Gly His Val Ala Cys Thr
65                  70                  75                  80

Tyr Ser Arg Ser Thr Leu Gly Gly Gln Gly Ser His Gly Glu His Ile
                85                  90                  95

Trp Leu Gln Lys Pro Pro Leu Lys Leu Ala Leu Leu Ser Leu Ala
            100                 105                 110
```

<210> SEQ ID NO 23
<211> LENGTH: 975
<212> TYPE: DNA
<213> ORGANISM: Mus musculus

<400> SEQUENCE: 23

```
ggccttctcc ttatgccttc cctgtgttca ctagagccat cccctgcct ccggaattcc     60 cacagatgga tcgctctgtg gcttcttaaa acttccctgc agggcactga ccctcagccc    120
```

```
ctctaagtca cttcttcccc agtgattgta cttttcaatc gggcttcaaa ctttcctctc      180
attaaatcag caagcacttt ccaagaaaag agagatgctc aagatgcctt cctgtgtgga      240
acaacgaagc ctaccctggt gctgctttgc tgtataggaa cctggctggc cacctgcagc      300
ttgtccttcg gtgccccaat atcgaaggaa gacttaagaa ctacaattga cctcttgaaa      360
caagagtctc aggatcttta taacaactat agcataaagc aggcatctgg gatgtcagca      420
gacgaatcaa tacagctgcc gtgtttcagc ctggaccggg aagcattaac caacatctcg      480
gtcatcatag cacatctgga gaaagtcaaa gtgttgagcg agaacacagt agatacttct      540
tgggtgataa gatggctaac aaacatcagc tgtttcaacc cactgaattt aaacatttct      600
gtgcctggaa atactgatga atcctatgat tgtaaagtgt tcgtgcttac ggttttaaag      660
cagttctcaa actgcatggc agaactgcag gctaaggaca atactacatg ctgagtgatg      720 ggggggggg ggtgcagtgt cctcagcagt gcctgtcctt cgagggctga gcttgcaacc      780
caggacttaa ctccaaaggg actgtgcggt cattactagt catgttattt atgtttttat      840
tttgtccact gaaatcttgt tctgctaccc tgtagggact ggaagtggca gctatattta      900
tttatttatg tactgagttt gttaacgctc catggaggag ccttcagagt ctatttaata      960
aattatattg acatg                                                       975
```

<210> SEQ ID NO 24
<211> LENGTH: 147
<212> TYPE: PRT
<213> ORGANISM: Rattus norvegicus

<400> SEQUENCE: 24

```
Met Gly Leu Ser Pro His Leu Ala Val Thr Leu Phe Cys Phe Leu Ile
1               5                   10                  15

Cys Thr Gly Asn Gly Ile His Gly Cys Asn Asp Ser Pro Leu Arg Glu
            20                  25                  30

Ile Ile Asn Thr Leu Asn Gln Val Thr Glu Lys Gly Thr Pro Cys Thr
        35                  40                  45

Glu Met Phe Val Pro Asp Val Leu Thr Ala Thr Arg Asn Thr Thr Glu
    50                  55                  60

Asn Glu Leu Ile Cys Arg Ala Ser Arg Val Leu Arg Lys Phe Tyr Phe
65                  70                  75                  80

Pro Arg Asp Val Pro Pro Cys Leu Lys Asn Lys Ser Gly Val Leu Gly
                85                  90                  95

Glu Leu Arg Lys Leu Cys Arg Gly Val Ser Gly Leu Asn Ser Leu Arg
            100                 105                 110

Ser Cys Thr Val Asn Glu Ser Thr Leu Thr Thr Leu Lys Asp Phe Leu
        115                 120                 125

Glu Ser Leu Lys Ser Ile Leu Arg Gly Lys Tyr Leu Gln Ser Cys Thr
    130                 135                 140

Ser Met Ser
145
```

<210> SEQ ID NO 25
<211> LENGTH: 140
<212> TYPE: PRT
<213> ORGANISM: Mus musculus

<400> SEQUENCE: 25

```
Met Gly Leu Asn Pro Gln Leu Val Val Ile Leu Leu Phe Phe Leu Glu
1               5                   10                  15

Cys Thr Arg Ser His Ile His Gly Cys Asp Lys Asn His Leu Arg Glu
```

```
                       20                  25                  30
Ile Ile Gly Ile Leu Asn Glu Val Thr Gly Glu Gly Thr Pro Cys Thr
            35                  40                  45

Glu Met Asp Val Pro Asn Val Leu Thr Ala Thr Lys Asn Thr Thr Glu
 50                  55                  60

Ser Glu Leu Val Cys Arg Ala Ser Lys Val Leu Arg Ile Phe Tyr Leu
65                  70                  75                  80

Lys His Gly Lys Thr Pro Cys Leu Lys Lys Asn Ser Ser Val Leu Met
                85                  90                  95

Glu Leu Gln Arg Leu Phe Arg Ala Phe Arg Cys Leu Asp Ser Ser Ile
            100                 105                 110

Ser Cys Thr Met Asn Glu Ser Lys Ser Thr Ser Leu Lys Asp Phe Leu
        115                 120                 125

Glu Ser Leu Lys Ser Ile Met Gln Met Asp Tyr Ser
    130                 135                 140

<210> SEQ ID NO 26
<211> LENGTH: 147
<212> TYPE: PRT
<213> ORGANISM: Mesocricetus auratus

<400> SEQUENCE: 26

Met Gly Leu Arg Pro Gln Leu Ala Ala Ile Leu Leu Cys Leu Leu Ala
1               5                   10                  15

Cys Thr Gly Asn Trp Thr Leu Gly Cys His His Gly Ala Leu Lys Glu
            20                  25                  30

Ile Ile His Ile Leu Asn Gln Val Thr Glu Lys Gly Thr Pro Cys Thr
        35                  40                  45

Glu Met Val Val Pro Asp Ala Leu Ser Ala Arg Lys Asn Ser Thr Glu
    50                  55                  60

Lys Asp Leu Ile Cys Arg Ala Ser Gln Gly Phe Arg Lys Phe Tyr Phe
65                  70                  75                  80

Gln His Glu Val Thr Leu Cys Leu Lys Asn Asn Ser Arg Val Leu Lys
                85                  90                  95

Asp Leu Lys Lys Leu Tyr Arg Gly Ile Ser Ser Leu Phe Pro Gln Lys
            100                 105                 110

Ser Cys Asn Val Asn Glu Ser Thr Tyr Thr Thr Leu Lys Asp Phe Leu
        115                 120                 125

Glu Ser Leu Arg Arg Ile Met Gln Lys Lys Tyr Trp Gln Cys Gly Ser
    130                 135                 140

Ser Thr Phe
145

<210> SEQ ID NO 27
<211> LENGTH: 143
<212> TYPE: PRT
<213> ORGANISM: Meriones unguiculatus

<400> SEQUENCE: 27

Met Gly Leu Ser Pro Gln Leu Ala Ala Val Leu Leu Cys Leu Leu Val
1               5                   10                  15

Cys Thr Gly Asn Tyr Ala Arg Arg Gln Asp Arg Glu Ala Gly Leu Arg
            20                  25                  30

Glu Ile Ile His Asn Leu Asp Gln Val Leu Lys Glu Thr Pro Cys
        35                  40                  45

Thr Glu Met Phe Val Pro Asp Val Leu Ile Ala Thr Lys Asn Thr Thr
    50                  55                  60
```

-continued

```
Glu Lys Gly Leu Leu Cys Arg Ala Thr Arg Val Leu Arg Lys Phe Tyr
 65                  70                  75                  80

Phe Pro Arg Glu Val Thr Pro Cys Leu Lys Asn Asn Ser Gly Val Leu
                 85                  90                  95

Ser Ile Leu Arg Lys Leu Cys Arg Ser Ile Ser Thr Leu His Pro Gln
            100                 105                 110

Glu Ser Cys Ser Val Ser Thr Pro Thr Leu Thr Thr Leu Asn Asp Phe
        115                 120                 125

Leu Gly Arg Leu Arg Gly Ile Met Gln Met Lys Asn Trp Gln Gly
    130                 135                 140

<210> SEQ ID NO 28
<211> LENGTH: 153
<212> TYPE: PRT
<213> ORGANISM: Cercocebus torquatus atys

<400> SEQUENCE: 28

Met Gly Leu Thr Ser Gln Leu Leu Pro Pro Leu Phe Phe Leu Leu Ala
 1               5                  10                  15

Cys Ala Gly Asn Phe Ala His Gly His Asn Cys His Ile Ala Leu Arg
                 20                  25                  30

Glu Ile Ile Glu Thr Leu Asn Ser Leu Thr Glu Gln Lys Thr Leu Cys
             35                  40                  45

Thr Lys Leu Thr Ile Thr Asp Ile Leu Ala Ala Ser Lys Asn Thr Thr
 50                  55                  60

Glu Lys Glu Thr Phe Cys Arg Ala Ala Thr Val Leu Arg Gln Phe Tyr
 65                  70                  75                  80

Ser His His Glu Lys Asp Thr Arg Cys Leu Gly Ala Ser Ala Gln Gln
                 85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Ser Gln Ser Thr Leu Glu Asp Phe Leu Glu Arg Leu Lys Thr Ile Met
    130                 135                 140

Arg Glu Lys Tyr Ser Lys Cys Ser Ser
145                 150

<210> SEQ ID NO 29
<211> LENGTH: 134
<212> TYPE: PRT
<213> ORGANISM: Equus caballus

<400> SEQUENCE: 29

Met Gly Leu Thr Tyr Gln Leu Leu Pro Ala Leu Val Cys Leu Leu Ala
 1               5                  10                  15

Cys Thr Ser Phe Ile Gln Gly Cys Lys Tyr Asp Ile Thr Leu Gln Glu
                 20                  25                  30

Ile Ile Lys Thr Leu Asn Leu Thr Asp Gly Lys Gly Lys Asn Ser Cys
             35                  40                  45

Met Glu Leu Thr Val Ala Asp Ala Phe Gly Pro Lys Asn Thr Asp Gly
 50                  55                  60

Lys Glu Ile Cys Arg Ala Ala Lys Val Lys Gln Gln Tyr Lys Arg His
 65                  70                  75                  80

Asp Arg Ser Leu Ile Lys Glu Cys Leu Ser Gly Leu Asp Arg Asn Leu
                 85                  90                  95
```

```
Lys Gly Met Ala Asn Gly Thr Cys Cys Thr Val Asn Glu Ala Lys Lys
                100                 105                 110

Ser Thr Leu Lys Asp Phe Leu Glu Arg Leu Lys Thr Ile Met Lys Glu
            115                 120                 125

Lys Tyr Ser Lys Cys Ser
        130
```

```
<210> SEQ ID NO 30
<211> LENGTH: 131
<212> TYPE: PRT
<213> ORGANISM: Mus musculus

<400> SEQUENCE: 30

Met Ala Leu Trp Val Thr Ala Val Leu Ala Leu Ala Cys Leu Gly Gly
1               5                   10                  15

Leu Ala Ala Pro Gly Pro Val Pro Arg Ser Val Ser Leu Pro Leu Thr
                20                  25                  30

Leu Lys Glu Leu Ile Glu Glu Leu Ser Asn Ile Thr Gln Asp Gln Thr
            35                  40                  45

Pro Leu Cys Asn Gly Ser Met Val Trp Ser Val Asp Leu Ala Ala Gly
        50                  55                  60

Gly Phe Cys Val Ala Leu Asp Ser Leu Thr Asn Ile Ser Asn Cys Asn
65                  70                  75                  80

Ala Ile Tyr Arg Thr Gln Arg Ile Leu His Gly Leu Cys Asn Arg Lys
                85                  90                  95

Ala Pro Thr Thr Val Ser Ser Leu Pro Asp Thr Lys Ile Glu Val Ala
            100                 105                 110

His Phe Ile Thr Lys Leu Leu Ser Tyr Thr Lys Gln Leu Phe Arg His
        115                 120                 125

Gly Pro Phe
        130
```

```
<210> SEQ ID NO 31
<211> LENGTH: 135
<212> TYPE: PRT
<213> ORGANISM: Ovis aries

<400> SEQUENCE: 31

Met Gly Leu Thr Ser Gln Leu Ile Pro Ala Leu Val Cys Leu Leu Val
1               5                   10                  15

Cys Thr Ser His Phe Val His Gly His Lys Cys Asp Ile Thr Leu Glu
                20                  25                  30

Glu Ile Ile Lys Thr Leu Asn Ile Leu Thr Ser Arg Lys Asn Ser Cys
            35                  40                  45

Met Glu Leu Pro Val Ala Asp Val Phe Ala Ala Pro Lys Asn Ala Thr
        50                  55                  60

Glu Lys Glu Thr Phe Cys Arg Ala Gly Ile Glu Leu Arg Arg Ile Tyr
65                  70                  75                  80

Arg Ser His Met Cys Leu Asn Lys Phe Leu Gly Gly Leu Asp Arg Asn
                85                  90                  95

Leu Ser Ser Leu Ala Ser Lys Thr Cys Ser Val Asn Glu Ala Lys Thr
            100                 105                 110

Ser Thr Ser Thr Leu Arg Asp Leu Leu Glu Arg Leu Lys Thr Ile Met
        115                 120                 125

Arg Glu Lys Tyr Ser Lys Cys
        130                 135
```

```
<210> SEQ ID NO 32
<211> LENGTH: 132
<212> TYPE: PRT
<213> ORGANISM: Homo sapiens

<400> SEQUENCE: 32

Met Ala Leu Leu Leu Thr Thr Val Ile Ala Leu Thr Cys Leu Gly Gly
1               5                   10                  15

Phe Ala Ser Pro Gly Pro Val Pro Pro Ser Thr Ala Leu Arg Glu Leu
            20                  25                  30

Ile Glu Glu Leu Val Asn Ile Thr Gln Asn Gln Lys Ala Pro Leu Cys
        35                  40                  45

Asn Gly Ser Met Val Trp Ser Ile Asn Leu Thr Ala Gly Met Tyr Cys
50                  55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
            85                  90                  95

Gly Gln Phe Ser Ser Leu His Val Arg Asp Thr Lys Ile Glu Val Ala
        100                 105                 110

Gln Phe Val Lys Asp Leu Leu Leu His Leu Lys Lys Leu Phe Arg Glu
    115                 120                 125

Gly Arg Phe Asn
130

<210> SEQ ID NO 33
<211> LENGTH: 650
<212> TYPE: DNA
<213> ORGANISM: Mus musculus

<400> SEQUENCE: 33
ggctccagag accacaggca aagcgggcct tcctcactct cttaccgtcg ccatgatctt    60
ccacacagga acaacgaagc ctaccctggt gctgctttgc tgtataggaa cctggctggc   120
cacctgcagc ttgtccttcg gtgccccaat atcgaaggaa gacttaagaa ctacaattga   180
cctcttgaaa caagagtctc aggatcttta taacaactat agcataaagc aggcatctgg   240
gatgtcagca gacgaatcaa tacagctgcc gtgtttcagc ctggaccggg aagcattaac   300
caacatctcg gtcatcatag cacatctgga gaaagtcaaa gtgttgagcg agaacacagt   360
agatacttct tgggtgataa gatggctaac aaacatcagc tgtttcaacc cactgaattt   420
aaacatttct gtgcctggaa atactgatga atcctatgat tgtaaagtgt tcgtgcttac   480
ggttttaaag cagttctcaa actgcatggc agaactgcag gctaaggaca atactacatg   540
ctgagtgatg ggggggggt gcagtgtcct cagcagtgcc tgtccttcga gggctgagct   600
tgcaacccag gacttaactc caaagggact gtgcggtcat tactagtcat            650

<210> SEQ ID NO 34
<211> LENGTH: 164
<212> TYPE: PRT
<213> ORGANISM: Homo sapiens

<400> SEQUENCE: 34

Met Ala Ser His Ser Gly Pro Ser Thr Ser Val Leu Phe Leu Phe Cys
1               5                   10                  15

Cys Leu Gly Gly Trp Leu Ala Ser His Thr Leu Pro Val Arg Leu Leu
            20                  25                  30

Arg Pro Ser Asp Asp Val Gln Lys Ile Val Glu Glu Leu Gln Ser Leu
        35                  40                  45
```

-continued

```
Ser Lys Met Leu Leu Lys Asp Val Glu Glu Lys Gly Val Leu Val
    50                  55                  60

Ser Gln Asn Tyr Thr Leu Pro Cys Leu Ser Pro Asp Ala Gln Pro Pro
65                  70                  75                  80

Asn Asn Ile His Ser Pro Ala Ile Arg Ala Tyr Leu Lys Thr Ile Arg
                85                  90                  95

Gln Leu Asp Asn Lys Ser Val Ile Asp Glu Ile Ile Glu His Leu Asp
            100                 105                 110

Lys Leu Ile Phe Gln Asp Ala Pro Glu Thr Asn Ile Ser Val Pro Thr
        115                 120                 125

Asp Thr His Glu Cys Lys Arg Phe Ile Leu Thr Ile Ser Gln Gln Phe
    130                 135                 140

Ser Glu Cys Met Asp Leu Ala Leu Lys Ser Leu Thr Ser Gly Ala Gln
145                 150                 155                 160

Gln Ala Thr Thr
```